United States Patent
Conner et al.

(10) Patent No.: US 7,963,991 B2
(45) Date of Patent: Jun. 21, 2011

(54) SPINAL IMPLANTS AND METHODS OF PROVIDING DYNAMIC STABILITY TO THE SPINE

(75) Inventors: E. Scott Conner, Santa Barbara, CA (US); Jeffrey Valko, San Clemente, CA (US)

(73) Assignee: Magellan Spine Technologies, Inc., Irvine, CA (US)

( * ) Notice: Subject to any disclaimer, the term of this patent is extended or adjusted under 35 U.S.C. 154(b) by 1126 days.

(21) Appl. No.: 11/726,664

(22) Filed: Mar. 21, 2007

(65) Prior Publication Data

US 2008/0071377 A1   Mar. 20, 2008

Related U.S. Application Data

(63) Continuation-in-part of application No. 11/398,434, filed on Apr. 5, 2006.

(60) Provisional application No. 60/711,714, filed on Aug. 26, 2005.

(51) Int. Cl.
*A61F 2/44* (2006.01)
(52) U.S. Cl. ................................. 623/17.11
(58) Field of Classification Search ..... 623/17.11–17.16
See application file for complete search history.

(56) References Cited

U.S. PATENT DOCUMENTS

| | | |
|---|---|---|
| 4,349,921 A | 9/1982 | Kuntz |
| 4,936,848 A | 6/1990 | Bagby |
| 5,015,247 A | 5/1991 | Michelson |
| 5,015,255 A | 5/1991 | Kushlich |
| 5,122,134 A | 6/1992 | Borzone et al. |
| 5,306,307 A | 4/1994 | Senter et al. |
| 5,390,683 A | 2/1995 | Pisharodi |
| 5,425,772 A | 6/1995 | Brantigan |
| 5,458,638 A | 10/1995 | Kuslich et al. |
| 5,484,437 A | 1/1996 | Michelson |
| 5,489,307 A | 2/1996 | Kushlich et al. |
| 5,499,984 A | 3/1996 | Steiner et al. |
| 5,653,761 A | 8/1997 | Pisharodi |
| 5,665,122 A | 9/1997 | Kambin |
| 5,720,749 A | 2/1998 | Rupp |
| 5,766,252 A | 6/1998 | Henry et al. |
| 5,865,847 A | 2/1999 | Kohrs et al. |
| 5,885,287 A | 3/1999 | Bagby |
| 5,947,971 A | 9/1999 | Kuslich et al. |
| 5,968,098 A | 10/1999 | Winslow |
| 6,080,155 A | 6/2000 | Michelson |
| 6,093,207 A | 7/2000 | Pisharodi |
| 6,117,174 A | 9/2000 | Nolan |
| 6,165,219 A | 12/2000 | Kohrs et al. |

(Continued)

*Primary Examiner* — Eduardo C Robert
*Assistant Examiner* — Elana B Fisher
(74) *Attorney, Agent, or Firm* — Robert D. Buyan; Stout, Uxa, Buyan & Mullins

(57) ABSTRACT

Spinal implants and methods to repair annular defects in intervertebral discs and provide dynamic stability to the spine in the vicinity of a repaired disc are described. Some implants include head and tail portions. In some embodiments, the head portion of an implant is enlarged relative to the tail portion. Some head portions and tail portions are adapted to support adjacent vertebrae and resist collapse of the intervertebral disc. Head portions provide a spacer function to maintain separation between adjacent vertebrae. A tapered portion of some implants engages end plates of adjacent vertebrae to resist forces tending to push the implant out of the intervertebral space. The tail portion of some implants includes a tail flange (which in some embodiments is of similar diameter to the head portion) that abuts extradiscal lips of the adjacent vertebrae and resists forces tending to push the implant deeper into the intervertebral space.

14 Claims, 27 Drawing Sheets

U.S. PATENT DOCUMENTS

| | | |
|---|---|---|
| 6,224,630 B1 | 5/2001 | Bao et al. |
| 6,245,107 B1 * | 6/2001 | Ferree .................. 606/279 |
| 6,283,966 B1 | 9/2001 | Houfburg |
| 6,309,421 B1 | 10/2001 | Pisharodi |
| 6,332,886 B1 | 12/2001 | Green et al. |
| 6,436,098 B1 | 8/2002 | Michelson |
| 6,436,102 B1 | 8/2002 | Ralph et al. |
| 6,447,548 B1 | 9/2002 | Ralph et al. |
| 6,460,853 B1 | 10/2002 | Knight |
| 6,471,725 B1 | 10/2002 | Ralph et al. |
| 6,482,235 B1 | 11/2002 | Lambrecht et al. |
| 6,500,206 B1 | 12/2002 | Bryan |
| 6,554,864 B2 | 4/2003 | Ralph et al. |
| 6,562,047 B2 | 5/2003 | Ralph et al. |
| 6,607,559 B2 | 8/2003 | Ralph et al. |
| 6,623,525 B2 | 9/2003 | Ralph et al. |
| 6,626,905 B1 | 9/2003 | Schmiel et al. |
| 6,663,637 B2 | 12/2003 | Dixon et al. |
| 6,689,125 B1 | 2/2004 | Keith et al. |
| 6,709,458 B2 | 3/2004 | Michelson |
| 6,723,128 B2 | 4/2004 | Uk |
| 6,733,531 B1 | 5/2004 | Trieu |
| 6,740,090 B1 | 5/2004 | Cragg et al. |
| 6,740,091 B2 | 5/2004 | Kohrs et al. |
| 6,743,234 B2 | 6/2004 | Burkus et al. |
| 6,770,074 B2 | 8/2004 | Michelson |
| 6,805,695 B2 | 10/2004 | Keith |
| 6,805,716 B2 | 10/2004 | Ralph et al. |
| 6,837,904 B2 | 1/2005 | Ralph et al. |
| 6,843,804 B2 | 1/2005 | Bryan |
| 6,875,213 B2 | 4/2005 | Michelson |
| 6,890,256 B2 | 5/2005 | Walker et al. |
| 6,923,810 B1 | 8/2005 | Michelson |
| 6,955,691 B2 | 10/2005 | Chae et al. |
| 6,984,247 B2 | 1/2006 | Cauthen |
| 7,004,970 B2 | 2/2006 | Cauthen et al. |
| 7,052,516 B2 | 5/2006 | Cauthen |
| 2002/0026192 A1 | 2/2002 | Schmiel et al. |
| 2002/0032448 A1 | 3/2002 | Houfburg |
| 2002/0123807 A1 | 9/2002 | Cauthen |
| 2002/0138144 A1 | 9/2002 | Michelson |
| 2002/0189622 A1 | 12/2002 | Cauthen et al. |
| 2003/0040796 A1 | 2/2003 | Ferree |
| 2003/0069586 A1 | 4/2003 | Errico et al. |
| 2003/0074075 A1 | 4/2003 | Thomas et al. |
| 2003/0074076 A1 | 4/2003 | Ferree et al. |
| 2003/0078579 A1 | 4/2003 | Ferree |
| 2003/0078590 A1 | 4/2003 | Errico et al. |
| 2003/0149483 A1 | 8/2003 | Michelson |
| 2003/0153976 A1 | 8/2003 | Cauthen et al. |
| 2003/0187508 A1 | 10/2003 | Cauthen |
| 2004/0002763 A1 | 1/2004 | Phillips et al. |
| 2004/0024407 A1 | 2/2004 | Ralph et al. |
| 2004/0024463 A1 | 2/2004 | Thomas et al. |
| 2004/0034429 A1 | 2/2004 | Lambrecht et al. |
| 2004/0039392 A1 * | 2/2004 | Trieu .................. 606/86 |
| 2004/0054413 A1 | 3/2004 | Higham et al. |
| 2004/0059420 A1 | 3/2004 | Michelson |
| 2004/0073217 A1 * | 4/2004 | Michelson .................. 606/61 |
| 2004/0078079 A1 | 4/2004 | Foley |
| 2004/0097980 A1 | 5/2004 | Ferree |
| 2004/0158325 A1 | 8/2004 | Errico et al. |
| 2004/0167628 A1 | 8/2004 | Foley |
| 2004/0210226 A1 | 10/2004 | Trieu |
| 2004/0260397 A1 | 12/2004 | Lambrecht et al. |
| 2005/0015151 A1 | 1/2005 | Fortin et al. |
| 2005/0043739 A1 | 2/2005 | Sullivan et al. |
| 2005/0071011 A1 | 3/2005 | Ralph et al. |
| 2005/0149197 A1 | 7/2005 | Cauthen |
| 2005/0154465 A1 | 7/2005 | Hodges et al. |
| 2005/0222681 A1 | 10/2005 | Richley et al. |
| 2005/0251146 A1 | 11/2005 | Martz et al. |
| 2005/0273111 A1 | 12/2005 | Ferree et al. |
| 2006/0015182 A1 | 1/2006 | Tsou |
| 2006/0089719 A1 | 4/2006 | Trieu |
| 2006/0100711 A1 | 5/2006 | Cauthen |
| 2006/0122704 A1 | 6/2006 | Vresilovic et al. |
| 2006/0129245 A1 | 6/2006 | Cauthen |
| 2006/0142864 A1 | 6/2006 | Cauthen |
| 2006/0155375 A1 | 7/2006 | Kagan et al. |
| 2006/0173545 A1 | 8/2006 | Cauthen et al. |
| 2006/0217747 A1 | 9/2006 | Ferree |
| 2006/0247778 A1 | 11/2006 | Ferree et al. |
| 2006/0253132 A1 | 11/2006 | Evans et al. |
| 2006/0253152 A1 | 11/2006 | Evans et al. |
| 2006/0287731 A1 | 12/2006 | Cauthen et al. |
| 2007/0043361 A1 | 2/2007 | Malandain et al. |
| 2007/0043374 A1 | 2/2007 | Evans |
| 2007/0050028 A1 | 3/2007 | Conner |
| 2007/0055375 A1 | 3/2007 | Ferree |
| 2007/0067040 A1 | 3/2007 | Ferree |
| 2007/0100354 A1 | 5/2007 | Cauthen et al. |
| 2007/0135920 A1 | 6/2007 | Ferree |
| 2007/0156152 A1 | 7/2007 | Ferree |
| 2007/0162062 A1 | 7/2007 | Norton et al. |
| 2007/0162131 A1 | 7/2007 | Friedman et al. |
| 2007/0168043 A1 | 7/2007 | Ferree |
| 2007/0198021 A1 | 8/2007 | Wales |

* cited by examiner

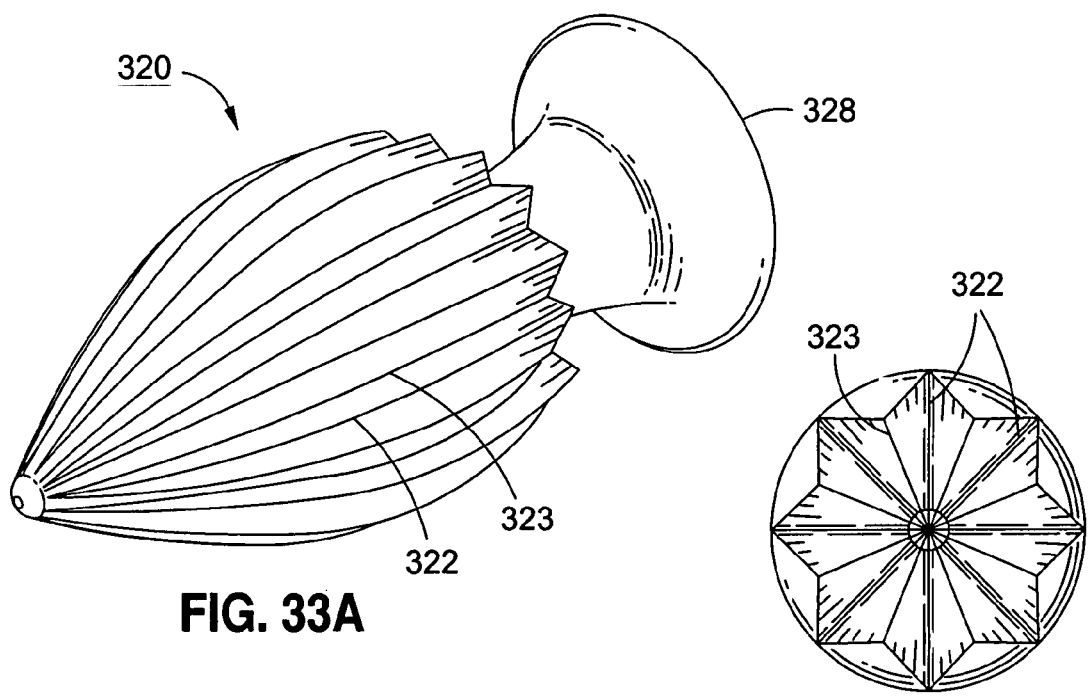
FIG. 33A
FIG. 33C
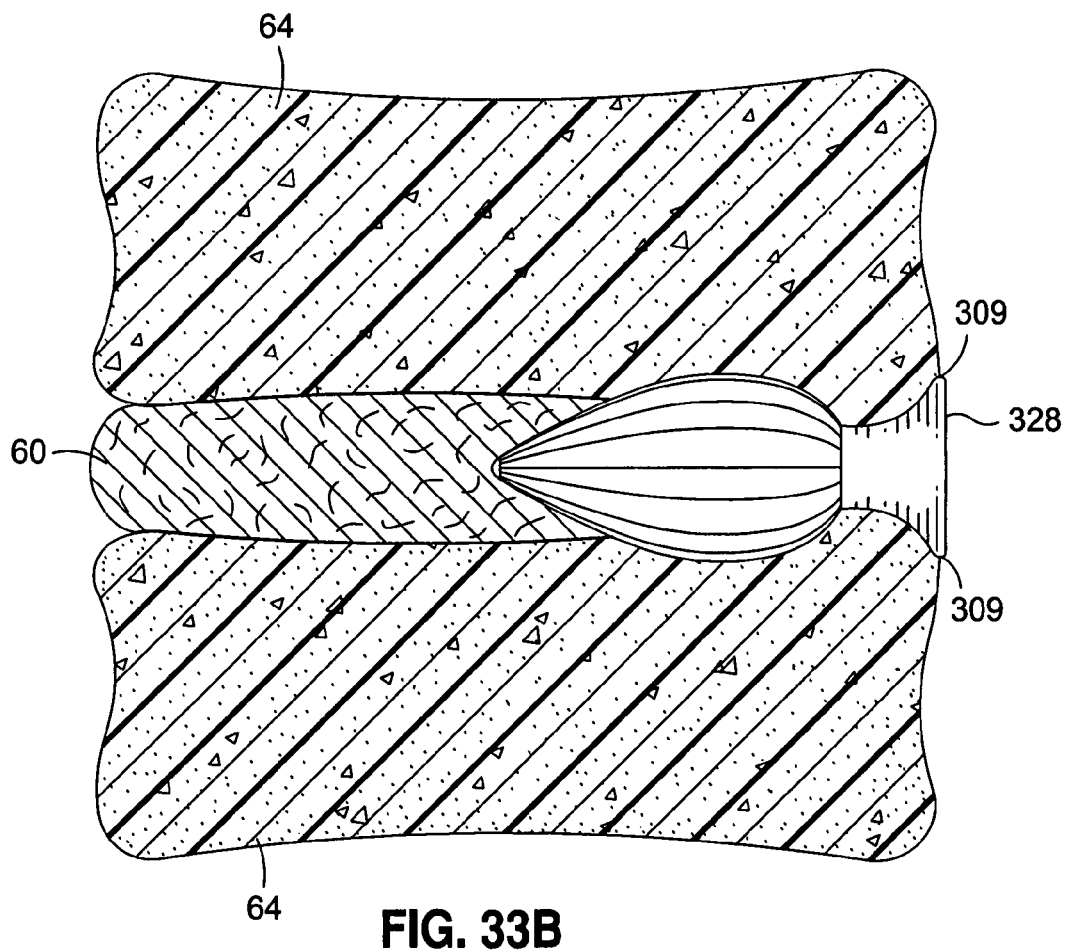
FIG. 33B

SPINAL IMPLANTS AND METHODS OF PROVIDING DYNAMIC STABILITY TO THE SPINE

RELATED APPLICATIONS

This application is a continuation-in-part of U.S. patent application Ser. No. 11/398,434, filed Apr. 5, 2006, which in turn claims priority from U.S. Provisional Application No. 60/711,714, filed on Aug. 26, 2005, the entire contents of these applications are herein incorporated by reference.

FIELD OF THE INVENTION

The present invention relates to devices and methods for repairing annular defects in intervertebral discs and for providing dynamic stability to the motion segment of the spine in the vicinity of the repaired disc.

BACKGROUND OF THE INVENTION

The vertebral spine is the axis of the skeleton upon which all of the body parts "hang." In humans, the normal spine has seven cervical, twelve thoracic and five lumbar segments. The lumbar segments sit upon a sacrum, which then attaches to a pelvis, in turn supported by hip and leg bones. The bony vertebral bodies of the spine are separated by intervertebral discs, which act as joints, but allow known degrees of flexion, extension, lateral bending and axial rotation.

Each intervertebral disc serves as a mechanical cushion between the vertebral bones, permitting controlled motions within vertebral segments of the axial skeleton. For example, FIG. 4 illustrates a healthy intervertebral disc 30 and adjacent vertebrae 32. A spinal nerve 34 extends along the spine posteriorly thereof.

The normal disc is a unique, mixed structure, comprised of three component tissues: The nucleus pulposus ("nucleus"), the annulus fibrosus ("annulus"), and two opposing vertebral end plates. The two vertebral end plates are each composed of thin cartilage overlying a thin layer of hard, cortical bone which attaches to the spongy, richly vascular, cancellous bone of the vertebral body. The end plates thus serve to attach adjacent vertebrae to the disc. In other words, a transitional zone is created by the end plates between the malleable disc and the bony vertebrae.

The annulus of the disc is a tough, outer fibrous ring that binds together adjacent vertebrae. This fibrous portion is generally about 10 to 15 mm in height and about 15 to 20 mm in thickness, although in diseased discs these dimensions can be diminished. The fibers of the annulus consist of 15 to 20 overlapping multiple plies, and are inserted into the superior and inferior vertebral bodies at roughly a 30 degree angle in both directions. This configuration particularly resists torsion, as about half of the angulated fibers will tighten when the vertebrae rotate in either direction, relative to each other. The laminated plies are less firmly attached to each other.

Immersed within the annulus, within the intervertebral disc space, is the nucleus pulposus. The annulus and opposing end plates maintain a relative position of the nucleus in what can be defined as a nucleus cavity. The healthy nucleus is largely a gel-like substance having high water content, and similar to air in a tire, serves to keep the annulus tight yet flexible. The nucleus-gel moves slightly within the annulus when force is exerted on the adjacent vertebrae with bending, lifting, etc.

Under certain circumstances, an annulus defect (or anulotomy) can arise that requires surgical attention. These annulus defects can be naturally occurring, surgically created, or both.

A naturally occurring annulus defect is typically the result of trauma or a disease process, and can lead to a disc herniation. FIG. 5 illustrates a herniated disc 36. A disc herniation occurs when the annulus fibers are weakened or torn and the inner tissue of the nucleus becomes permanently bulged, distended, or extruded out of its normal, internal annular confines. The mass of a herniated or "slipped" nucleus 38 can compress a spinal nerve 40, resulting in leg pain, loss of muscle control, or even paralysis.

Where the naturally occurring annulus defect is relatively minor and/or little or no nucleus tissue has escaped from the nucleus cavity, satisfactory healing of the annulus can be achieved by immobilizing the patient for an extended period of time. However, many patients require surgery (microdiscectomy) to remove the herniated portion of the disc. FIG. 6 illustrates a disc from which a portion has been removed through a microdiscectomy procedure. After the traditional microdiscectomy, loss of disc space height can also occur because degenerated disc nucleus is removed as part of the surgical procedure. Loss of disc space height can also be a source of continued or new lumbar spine generated pain.

Further, a more problematic annulus defect concern arises in the realm of anulotomies encountered as part of a surgical procedure performed on the disc space. Alternatively, with discal degeneration, the nucleus loses its water binding ability and deflates, as though the air had been let out of a tire. Subsequently, the height of the nucleus decreases, causing the annulus to buckle in areas where the laminated plies are loosely bonded. As these overlapping laminated plies of the annulus begin to buckle and separate, either circumferential or radial annular tears can occur, which can contribute to persistent and disabling back pain. Adjacent, ancillary spinal facet joints will also be forced into an overriding position, which can create additional back pain.

In many cases, to alleviate pain from degenerated or herniated discs, the nucleus is removed and the two adjacent vertebrae surgically fused together. While this treatment can alleviate the pain, all discal motion is lost in the fused segment. Ultimately, this procedure places greater stress on the discs adjacent the fused segment as they compensate for the lack of motion, perhaps leading to premature degeneration of those adjacent discs.

SUMMARY OF THE INVENTION

In contrast to prior art methods of performing annular repairs, it would be desirable to replace, in whole or in part, the damaged intervertebral disc, with a suitable prosthesis having the ability to complement the normal height and motion of the disc while stimulating the natural disc physiology.

The preferred embodiments of the present spinal implants and methods of providing dynamic stability to the spine have several features, no single one of which is solely responsible for their desirable attributes. Without limiting the scope of these spinal implants and methods as expressed by the claims that follow, their more prominent features will now be discussed briefly. After considering this discussion, and particularly after reading the section entitled "Detailed Description of the Invention", one will understand how the features of the preferred embodiments provide advantages, which include, inter alia, the capability to repair annular defects and stabilize adjacent motion segments of the spine without substantially diminishing the range of motion of the spine, simplicity of structure and implantation, and a low likelihood that the implant will migrate from the implantation site.

In some embodiments there is provided a spinal implant adapted to repair an annular defect in the annulus fibrosus of an intervertebral disc, located in an intervertebral disc space between adjacent vertebrae of a spine, the implant comprising: a head portion, comprising a first head segment having a length greater than zero as measured along a longitudinal axis of the implant and having a substantially constant height along its length; and a tail portion, including a first tail segment and a second tail segment, the first tail segment coupled to the head portion, the second tail segment being.

Configured to prevent substantial extrusion of intervertebral disc material through the annular defect when the head portion is positioned between the adjacent vertebrae and when the second tail segment contacts a surface of the annulus fibrosus and spans a width of the annular defect.

In some embodiments of the spinal implant the second tail segment is configured to abut at least one of the extradiscal lips of the adjacent vertebrae, and to abut the annulus fibrosus, when the head portion is positioned between the adjacent vertebrae. In some embodiments the second tail segment is configured to contact an outer surface of the annulus fibrosus.

In some embodiments the first tail segment is reversibly coupled to the head portion. In some embodiments the first tail segment is lockably coupled to the head portion.

In some embodiments of the spinal implant the head portion further comprises a second head segment that is adjacent the first head segment and that has a length greater than zero as measured along a longitudinal axis of the implant, the second head segment tapering along at least a portion of its length from a greater height to a lesser height away from the first head segment.

In some embodiments there is provided a method of providing dynamic stability to the spine in the vicinity of an intervertebral disc, the method comprising the steps of: removing bone material from at least one of the endplates of either or both of adjacent first and second vertebrae, thereby shaping a portion of the at least one of the adjacent first and second vertebrae to create an implantation site that is sized and shaped to receive a spinal implant in a substantially complementary fit; and implanting the spinal implant device at the implantation site such that it contacts the first and second vertebrae in the substantially complementary fit.

In some embodiments the method further comprises removing bone material from the two facing endplates of the adjacent first and second vertebrae. In some embodiments the method further comprises countersinking the implantation site to remove bone material from each of the first and second vertebrae.

In some embodiments a spinal implant adapted to repair an annular defect in the annulus fibrosus of an intervertebral disc, located between adjacent vertebrae of a spine comprises: a head portion configured to be placed between the adjacent vertebrae, the head portion comprising a buttress portion that, when positioned between the adjacent vertebrae, spans a distance between, and contacts, the adjacent vertebrae; and a barrier portion having a width that is greater than a width of the annular defect, the barrier portion being configured to prevent substantial extrusion of intervertebral disc material through the annular defect when the barrier portion is positioned to contact a surface of the annulus fibrosus; wherein the head portion is coupled to the barrier portion.

In some embodiments the surface of the annulus fibrosus is an outer surface.

In some embodiments of a spinal implant the head portion is reversibly coupled to the barrier portion. In some embodiments of a spinal implant the head portion is lockably coupled to the barrier portion.

In some embodiments of the spinal implant the head portion has a section having a substantially constant height that is approximately equal to the distance between the adjacent vertebrae.

In some embodiments of the spinal implant upon implantation within the intervertebral disc space between the adjacent vertebrae: the head portion abuts and supports facing endplates of adjacent vertebrae to aid in preventing at least partial collapse of the intervertebral disc; and the barrier portion abuts at least one of the extradiscal lips of the adjacent vertebrae, thereby substantially preventing the barrier portion from entering into the intervertebral disc space.

In some embodiments of the a height of the head portion is adapted such that the head portion operates as a spacer to maintain a desired separation distance between the adjacent vertebrae.

In some embodiments of the spinal implant a cross-section of the implant taken along a longitudinal axis thereof is at least one of circular, oval, elliptical, and rectilinear.

In some embodiments the spinal implant comprises at least one of bone, a polymer, and a metal.

In some embodiments the spinal implant further comprises a lumen passing therethrough. In some embodiments the lumen is adapted to receive an elongate member. In some embodiments the elongate member comprises a guide wire.

In some embodiments the spinal implant further comprises splines that engage opposing surfaces of the adjacent vertebrae.

In some embodiments of the spinal implant, the head portion and the barrier portion are coupled by a flexible tether.

In some embodiments the spinal implant further comprises a threaded portion that engages opposing surfaces of the adjacent vertebrae.

In some embodiments the spinal implant further comprises barbs that engage opposing surfaces of the adjacent vertebrae.

In some embodiments of the spinal implant, the head portion and barrier portion comprise different materials.

In some embodiments there is provided a system for use in the repair of an annular defect in the annulus fibrosus of an intervertebral disc, located between adjacent vertebrae of a spine, comprising: a spinal implant comprising a head portion configured to be placed between the adjacent vertebrae; a barrier portion having a width that is greater than a width of the annular defect; an elongate member adapted to pass through a lumen of the spinal implant; wherein the head portion comprises a buttress portion that, when positioned between the adjacent vertebrae, spans a distance between, and contacts, the adjacent vertebrae; wherein the barrier portion is configured to prevent substantial extrusion of intervertebral disc material through the annular defect when the barrier portion is positioned to contact a surface of the annulus fibrosus; wherein the head portion is coupled to the barrier portion; wherein an elongate member passes through said lumen of said head portion and said barrier portion, wherein the elongate member is adapted to direct the spinal implant toward the annular defect.

In some embodiments of the system, the elongate member comprises a surgical guide wire.

In some embodiments of the system, the head portion is reversibly coupled to the barrier portion. In some embodiments of the system, the head portion is lockably coupled to the barrier portion.

In some embodiments there is provided a spinal implant adapted to repair an annular defect in the annulus fibrosus of an intervertebral disc, located between adjacent vertebrae of a spine, the implant comprising: means for maintaining a separation distance between the adjacent vertebrae; and means for preventing substantial extrusion of intervertebral disc material through the annular defect when the means for preventing is positioned to contact a surface of the annulus fibrosus and when the means for maintaining is positioned between the adjacent vertebrae; wherein the means for maintaining is coupled to the means for preventing.

In some embodiments there is provided a spinal implant adapted to repair an annular defect in the annulus fibrosus of an intervertebral disc, located between adjacent vertebrae of a spine, the implant comprising: a head portion including at least a first head segment and a second head segment, each of the first and second head segments having a length greater than zero as measured along a longitudinal axis of the implant, the first head segment having a constant height along its length, the second head segment tapering along as least a portion of its length from a greater height to a lesser height away from the first head segment; a tail portion extending from the head portion and including at least a first tail segment and a second tail segment, the first tail segment adjoining the second head segment, each of the first and second tail segments having a length greater than zero as measured along a longitudinal axis of the implant, the second tail segment tapering along at least a portion of its length from a lesser height to a greater height away from the first tail segment.

In some embodiments the head portion is reversibly coupled to the barrier portion. In some embodiments the head portion is lockably coupled to the barrier portion.

In some embodiments of the implant the second tail segment is configured to contact an outer surface of the annulus fibrosus.

In some embodiments of the spinal implant, upon implantation within the intervertebral disc space between the adjacent vertebrae: the head portion abuts and supports facing endplates of adjacent vertebrae to aid in preventing at least partial collapse of the intervertebral disc; and the tail portion abuts at least one of the extradiscal lips of the adjacent vertebrae, thereby substantially preventing the barrier portion from entering into the intervertebral disc space.

In some embodiments there is provided a spinal implant adapted to repair an annular defect in the annulus fibrosus of an intervertebral disc, located between adjacent vertebrae of a spine, the implant comprising: a head portion, comprising a first head segment having a length greater than zero as measured along a longitudinal axis of the implant and having a substantially constant height along its length; a tail portion extending from the head portion and including at least a first tail segment and a second tail segment, the first tail segment adjoining the second head segment, each of the first and second tail segments having a length greater than zero as measured along a longitudinal axis of the implant, the second tail segment tapering along at least a portion of its length from a lesser height to a greater height away from the first tail segment In some embodiments, the head portion is reversibly coupled to the barrier portion. In some embodiments, the head portion is lockably coupled to the barrier portion.

In some embodiments, the second tail segment is configured to contact an outer surface of the annulus fibrosus.

In some embodiments of the spinal implant, upon implantation within the intervertebral disc space between the adjacent vertebrae: the head portion abuts and supports facing endplates of adjacent vertebrae to aid in preventing at least partial collapse of the intervertebral disc; and the tail portion abuts at least one of the extradiscal lips of the adjacent vertebrae, thereby substantially preventing the barrier portion from entering into the intervertebral disc space.

In some embodiments there is provided a spinal implant adapted to repair an annular defect in the annulus fibrosus of an intervertebral disc, located between adjacent vertebrae of a spine, the implant comprising: a head portion including at least a first head segment and a second head segment, each of the first and second head segments having a length greater than zero as measured along a longitudinal axis of the implant, the first head segment having a constant height along its length, the second head segment tapering along as least a portion of its length from a greater height to a lesser height away from the first head segment; a barrier portion having a width that is greater than a width of the annular defect, the barrier portion being configured to prevent substantial extrusion of intervertebral disc material through the annular defect when the barrier portion is positioned to contact a surface of the annulus fibrosus; wherein the head portion is coupled to the barrier portion.

In some embodiments the head portion is reversibly coupled to the barrier portion. In some embodiments the head portion is lockably couple to the barrier portion.

In some embodiments the barrier portion is configured to contact an outer surface of the annulus fibrosus In some embodiments of the spinal implant, upon implantation within the intervertebral disc space between the adjacent vertebrae: the head portion abuts and supports facing endplates of adjacent vertebrae to aid in preventing at least partial collapse of the intervertebral disc; and the barrier portion abuts at least one of the extradiscal lips of the adjacent vertebrae, thereby substantially preventing the barrier portion from entering into the intervertebral disc space.

In some embodiments there is provided a method of repairing an annular defect in the annulus fibrosus of an intervertebral disc, located between adjacent vertebrae of a spine, the method comprising: providing a spinal implant, comprising: a head portion configured to be placed between the adjacent vertebrae, the head portion comprising a buttress portion that, when positioned between the adjacent vertebrae, spans a distance between, and contacts, the adjacent vertebrae; and a barrier portion having a width that is greater than a width of the annular defect, the barrier portion being configured to prevent substantial extrusion of intervertebral disc material from the intervertebral disc when the barrier portion is positioned to contact a surface of the annulus fibrosus; wherein the head portion is coupled to the barrier portion; and positioning the head portion between the adjacent vertebrae; and positioning the implant between the adjacent vertebrae.

In some embodiments, the implant further comprises a lumen passing therethrough, and the positioning of the implant comprises moving the implant along an elongate member, which passes through the lumen.

In some embodiments, the elongate member comprises a guide wire.

BRIEF DESCRIPTION OF THE DRAWINGS

The preferred embodiments of the present spinal implants and methods of providing dynamic stability to the spine, illustrating their features, will now be discussed in detail. These embodiments depict the novel and non-obvious spinal implants and methods shown in the accompanying drawings, which are for illustrative purposes only. These drawings include the following figures, in which like numerals indicate like parts.

FIG. 33 illustrates a front perspective view of a hollow splined spinal implant with (A), the device implanted within the disc (B), and a front view of the implant (C).

DETAILED DESCRIPTION OF THE INVENTION

In general, embodiments of the present spinal implant comprise a head portion and a barrier portion. The head portion is configured to be placed between adjacent vertebrae at the site of an annular defect. The head portion includes a buttress portion that when positioned in the intervertebral space, spans a distance between, and contacts, adjacent vertebrae. The head portion is further operative as a spacer to maintain a desired separation distance between the adjacent vertebrae.

Coupled to the head portion is a barrier portion. The barrier portion has a width that is greater than the width of the annular defect. The barrier portion is configured to prevent substantial extrusion of nucleus pulposus from the intervertebral disc when the barrier portion is positioned to contact an out surface of the annulus fibrosis, and spans the width of the annular defect.

The barrier portion can be further understood as including a tail portion and a tail flange portion, as is illustrated in the accompanying figures.

Figure 1:
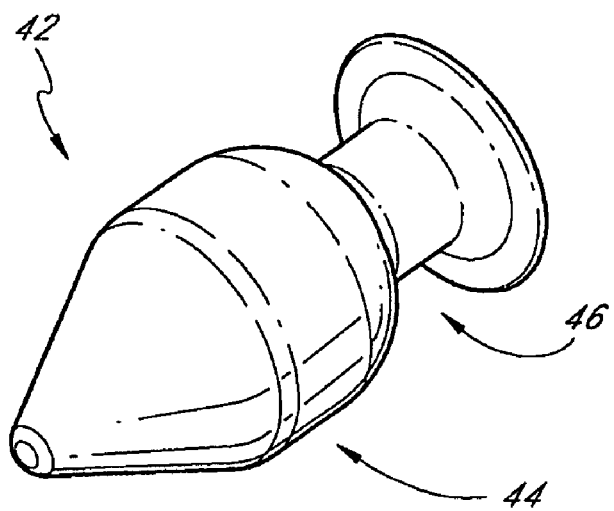
FIG. 1 is a front perspective view of one embodiment of the present spinal implants.
Figure 2:
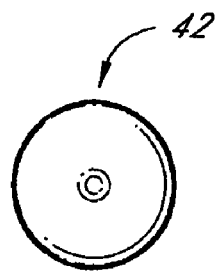
FIG. 2 is a front elevational view of the spinal implant of FIG. 1.
Figure 3:
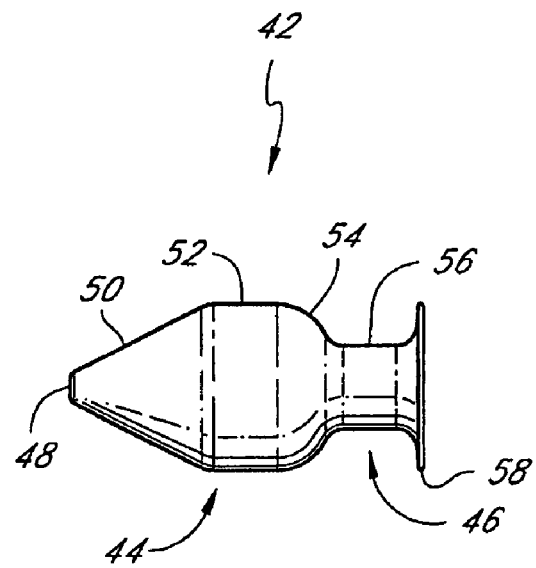
FIG. 3 is a right-side elevational view of the spinal implant of FIG. 1.
Figure 4:
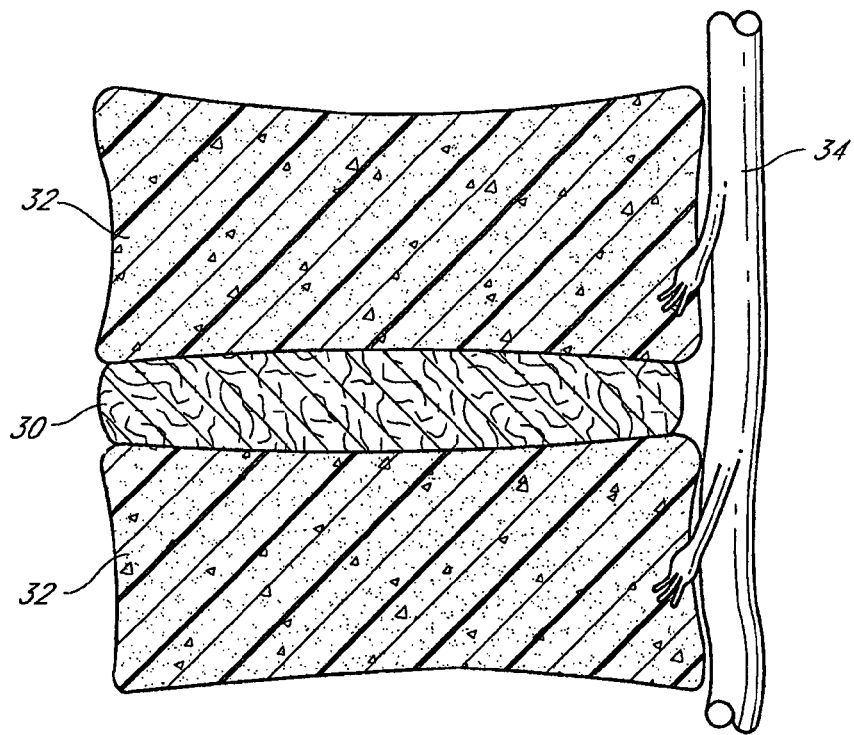
FIG. 4 is a right-side elevational view of a normal intervertebral disc, the adjacent vertebrae and a spinal nerve.
Figure 5:
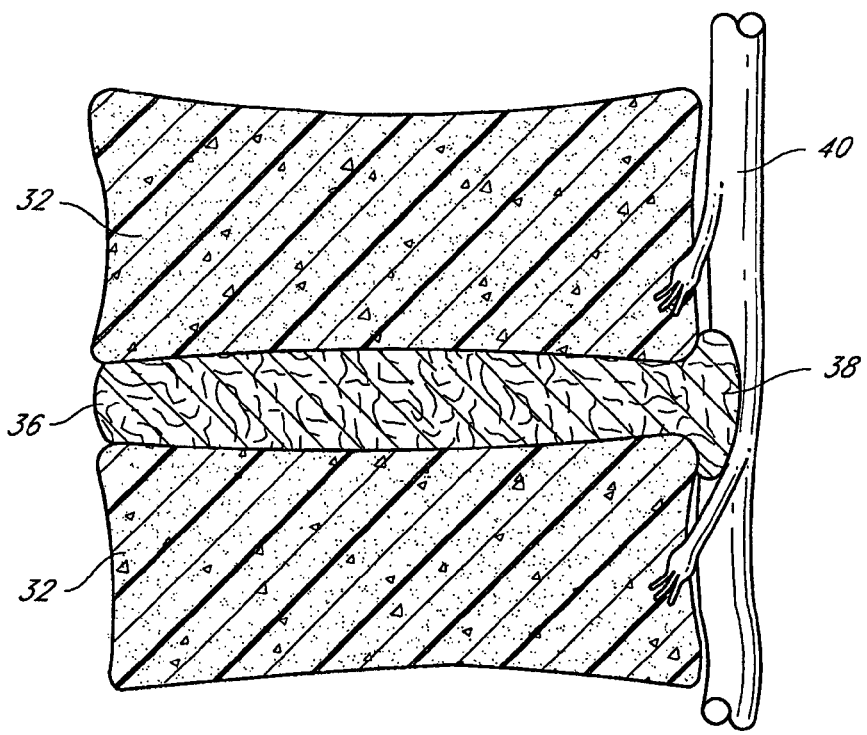
FIG. 5 is a right-side elevational view of a herniated intervertebral disc, the adjacent vertebrae and a spinal nerve.

FIGS. 1-3 illustrate an embodiment of the present spinal implants. The implant 42 is shaped as a contoured plug having an enlarged head portion 44 and a relatively narrow tail portion 46 (FIG. 3). In the illustrated embodiment, cross-sections taken perpendicularly to a longitudinal axis of the implant 42 are all substantially circular. However, the area of a given cross-section varies along the longitudinal axis.

With reference to FIG. 3, the head portion 44 comprises a tapered distal segment DS, a middle segment MS and a proximal surface PS. As seen in the side view of FIG. 3, the distal segment DS of the head portion 44 has non-parallel upper and lower ed es UE, LE that are closer together at their distal ends than at their proximal ends. The middle segment MS of the head portion 44 has an upper edge UE and a lower edge LE that are parallel to one another. In the non-limiting example of FIGS. 1-3, the head portion 44 includes a substantially flat nose 48 at a first end of a conical segment 50. The conical segment increases in height and cross-sectional area at a substantially constant rate from the nose to a first end of a large cylindrical segment 52. The large cylindrical segment extends at a constant height and cross-sectional area from the conical segment to a first end of a tapered segment 54. The tapered segment decreases in height and cross-sectional area at an increasing rate from the large cylindrical segment to a first end of a small cylindrical segment 56. The small cylindrical segment is substantially smaller in diameter than the large cylindrical segment, and extends at a constant height and cross-sectional area from the tapered segment to a tail flange 58. The tail flange flares outwardly from a minimum height and cross-sectional area at a second end of the small cylindrical segment to a maximum height and cross-sectional area at a second end of the implant 42. The maximum height of the tail flange is approximately equal to that of the large cylindrical segment.

The illustrated shape of the implant 42, including the relative dimensions of the segments 50, 52, 54, 56 and the flange 58, is merely one example. For example, cross-sections of the implant 42 taken along the longitudinal axis can be oval or elliptical or rectangular instead of circular. The ratio of the diameter of the small cylindrical segment 56 to the diameter of the large cylindrical segment 52 can be lesser or greater, for example. Also, the implant 42 need not include the substantially cylindrical segments 52, 56. For example, the implant 42 can continue to taper from the nose 48 all the way to the tapered segment 54, and the small cylindrical segment 56 can be reshaped to resemble adjoining tapered segments joined by a neck of a minimum diameter. Furthermore, the anatomy of annular defects and of vertebral end plates has wide variations. Accordingly, the implant 42 can be manufactured in a variety of shapes and sizes to fit different patients. A plurality of differently sized implants can, for example, be available as a kit to surgeons so that during an implantation procedure a surgeon can select the proper size implant from a range of size choices. FIGS. 14-22, described in more detail below, illustrate implants having sample alternative shapes and sizes.

The implant 42 is preferably constructed of a durable, biocompatible material. For example, bone, ceramic, polymer or metal can be used. Examples of suitable polymers include, but are not limited to, silicone, polyethylene, polycarbonate, polysulfone, polypropylene, polyetheretherketone, polyetheretherketone resins, etc. Examples of suitable metals for constructing the implant 42 include, but are not limited to, stainless steel alloys, titanium and titanium alloys, cobalt nickel alloys, nickel titanium alloys, tantalum, and the like.

In some embodiments, the material is non-compressible, so that the implant 42 can provide dynamic stability to the motion segment, as explained in detail below. In certain other embodiments, the material can be compressible. In some embodiments the material can be elastomeric, and the structure fabricated therefrom can be compressible. In some embodiments the structure can be compressible vertically, in order to resist forces imposed by spinal compression, but relatively incompressible laterally. The choice of materials most suitable to provide resilience, compressibility or elastic properties will b readily apparent to those skilled in the art, and thus the choice of material from which the implant can be constructed is not intended to limit the scope of the invention.

Figure 6:
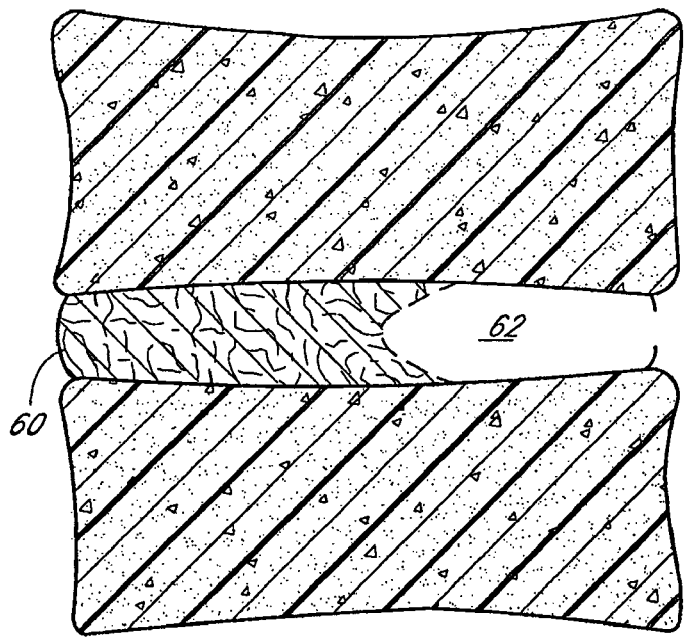
FIG. 6 is a right-side elevational view of the disc of FIG. 5 after a microdiscectomy procedure.
Figure 7:
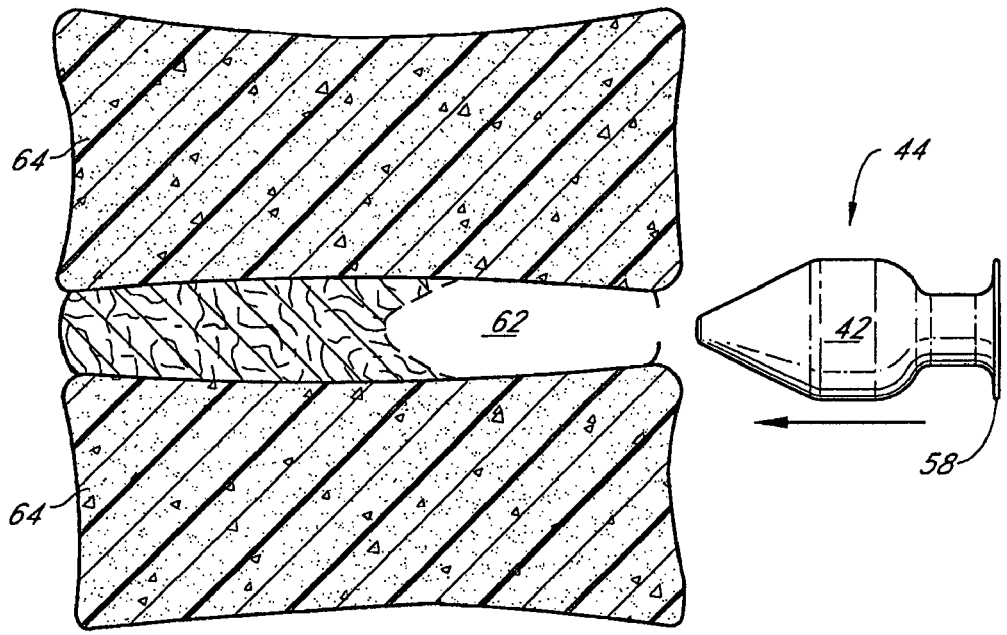
FIG. 7 is a right-side elevational view of the disc of FIG. 6 and the implant of FIG. 1.
Figure 8:
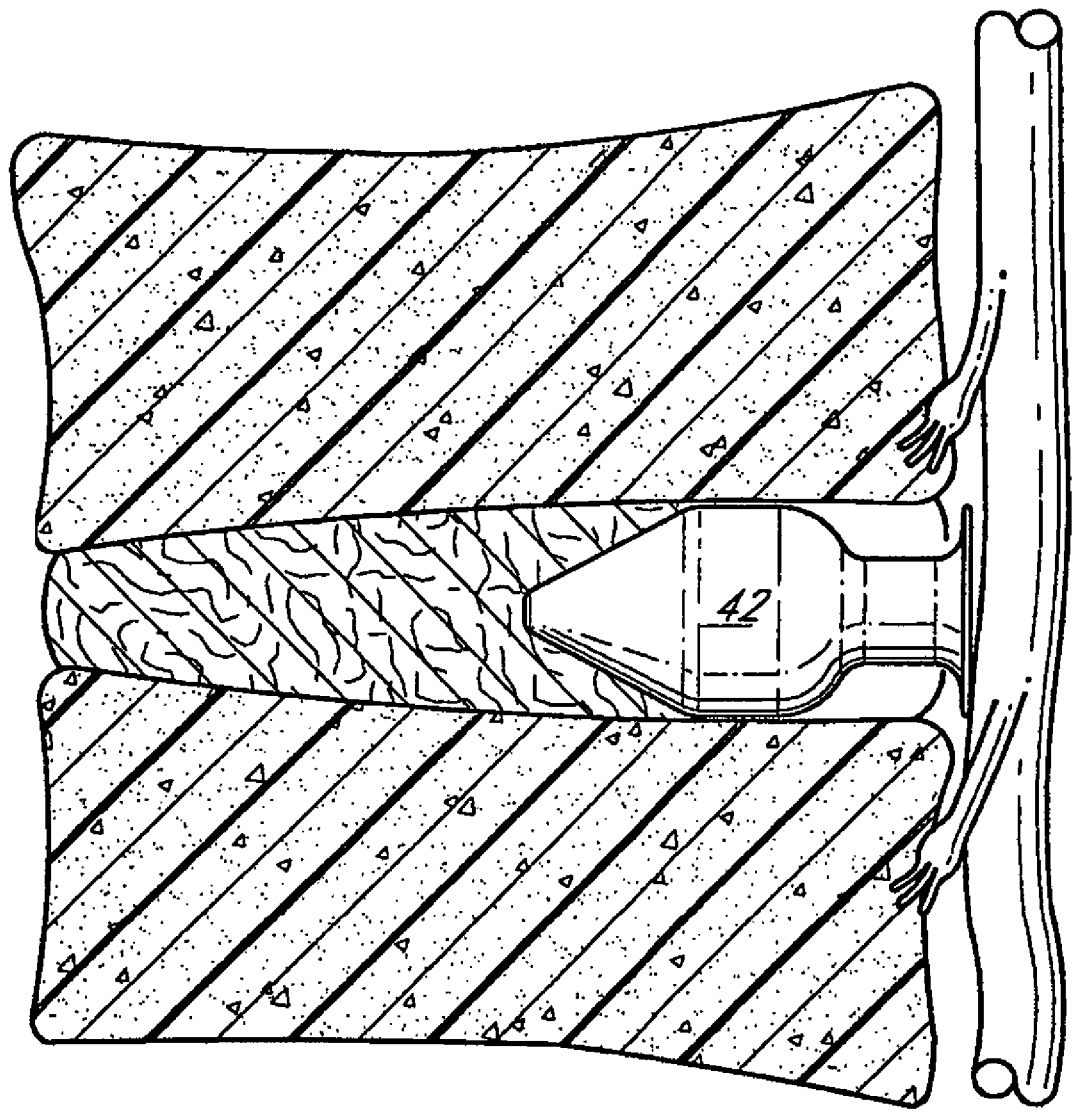
FIG. 8 is a right-side elevational view of the disc and the implant of FIG. 7, showing the implant implanted within the disc.

FIG. 6 illustrates an intervertebral disc 60 that has undergone a microdiscectomy procedure. A portion of the disc nucleus has been removed leaving a void 62. As shown in FIGS. 7 and 8, the implant 42 is adapted to be inserted between adjacent vertebrae 64 to fill the void 62. Once implanted, the contoured body of the implant 42, including the enlarged head portion 44 and the relatively narrow tail portion 46, can provide support to the adjacent vertebrae 64, resisting any tendency of these vertebrae to move closer to one another. However, in many cases the adjacent vertebrae 64 are not naturally shaped to provide mating engagement with the implant 42. As FIG. 8 shows, the implant 42 can sometimes be too large to fit within the intervertebral space, causing the adjacent vertebrae 64 to be forced apart.

To avoid the ill fitting engagement shown in FIG. 8, FIGS. 9-13 illustrate one embodiment of a method for implanting the implant 42 of FIGS. 1-3. In these figures, a portion of the intervertebral disc 60 has been removed through a microdiscectomy procedure. Before any disc material is removed, the implanting physician can visualize the implantation site using, for example, magnetic resonance imaging, or any other visualization technique. The visualization step allows the physician to determine what size and shape of implant is best suited to the procedure, which in turn allows the physician to determine what size and shape of tools to use during the procedure.

Before the implant 42 is introduced, the intervertebral space 62 and the adjacent vertebrae 64 can be prepared so that the implant 42 will fit properly. For example, each of the adjacent vertebrae 64 includes an end plate 66. In a healthy spine, these end plates abut the intervertebral discs. In the spine of FIGS. 9-13, these end plates will abut the implant 42 after it is implanted. Accordingly, the end plates can be shaped so that they have a mating or complementary fit with respect to the contoured implant 42 and enable the implant 42 to maintain its desired position within the intervertebral space.

Figure 9:
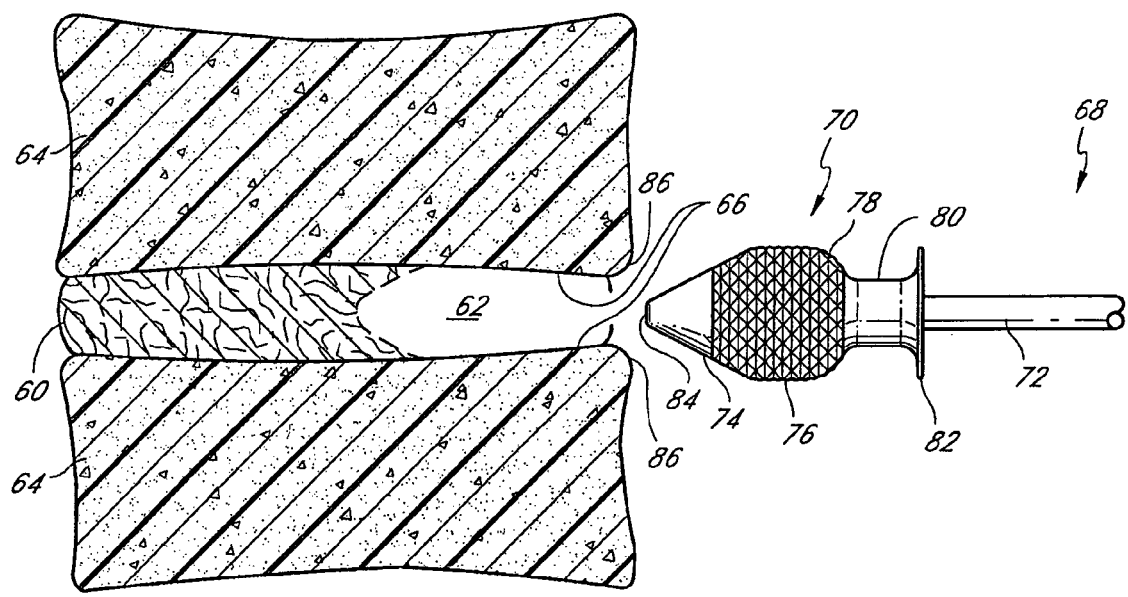
FIG. 9 is a right-side elevational view of the disc of FIG. 6 and one embodiment of a reaming tool that can be used during a procedure to implant the implant of FIG. 1.

FIG. 9 illustrates one embodiment of a reaming tool 68 that is adapted to shape the end plates 66 of adjacent vertebrae 64. The reaming tool 68 includes a head portion 70 that extends from a distal end of a shaft 72. The head portion 70 and the shaft 72 can be formed integrally with one another, or the head portion 70 can be secured to the shaft 72 by any known means. The head portion and shaft are preferably rigid, and can be made of a metal, for example. In the illustrated embodiment, the head portion is shaped substantially the same as the implant 42, and includes a conical segment 74, a large cylindrical segment 76, a tapered segment 78, a small cylindrical segment 80 and a tail flange 82. Those of ordinary skill in the art will appreciate that the illustrated size and shape of the head portion 70 is merely an example. However, it is advantageous for the head portion to be of similar size and shape to the implant that will ultimately be implanted in the intervertebral space 62 (whether that size and shape is the same as or different from the implant 42 of FIGS. 1-3).

At least a leading portion of the conical segment 74 includes a smooth outer surface. This smooth surface facilitates the entry of the head portion 70 into the intervertebral space 62, as described below. The small cylindrical segment 80 and tail flange 82 also each include a smooth outer surface. A trailing portion of the conical segment 74, the large cylindrical segment 76 and the tapered segment 78 each include a roughened surface. This surface can, for example, be knurled or burred. The roughened surface is adapted to remove bone from the vertebral end plates 66 in order to reshape the end plates so that they have a mating or complementary fit with respect to the contoured implant 42. In other embodiments, fewer, or more, segments of the head portion 70 can be roughened in order to provide desired capabilities for shaping the end plates 66.

To insert the head portion 70 into the intervertebral space 62, the surgeon positions the nose 84 of the head portion adjacent the extradiscal lips 86 on the adjacent vertebrae 64, as shown in FIG. 9. Then, applying digital pressure along the longitudinal axis of the shaft 72, the surgeon can push the head portion 70 into the void 62 between the adjacent vertebrae. Alternatively, the surgeon can strike a proximal end of the shaft 72 with a mallet to drive the head portion 70 into the void 62. The head portion 70 forces the adjacent vertebrae 64 apart as it penetrates. Often, the adjacent vertebrae are resistant to being forced apart and significant force must be applied along the axis of the shaft 72 to force the head portion 70 into the void 62. The smooth surface at the leading end of the conical portion 74, which reduces friction between the head portion and the extradiscal lips 86, facilitates the entry of the head portion into the comparatively small void 62.

Figure 10:
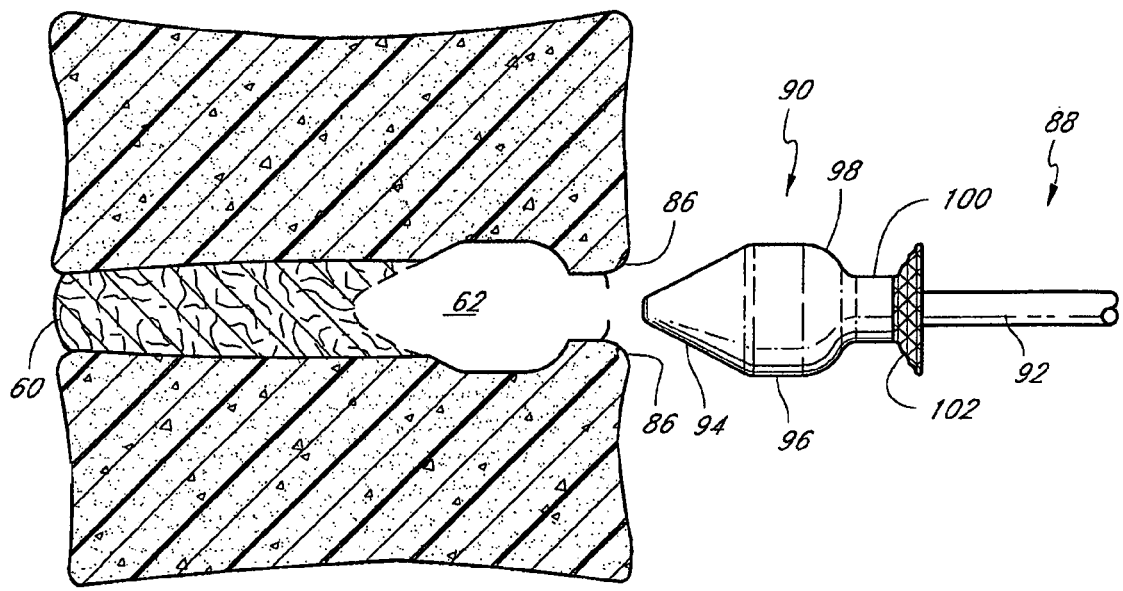
FIG. 10 is a right-side elevational view of the disc of FIG. 9 after the reaming step, and a countersinking tool that can be used during a procedure to implant the implant of FIG. 1.

To remove material from the end plates 66, the surgeon rotates the shaft 72. The rotational force to the shaft can be applied directly by grasping the shaft with one's fingers, or by using a gripping instrument. Alternatively, a proximal end of the shaft can engage a powered or manual drill, which can impart a rotational force to the shaft. The rotating shaft 72 rotates the head portion so that the roughened surfaces on the conical portion 74, the large cylindrical segment 76 and the tapered segment 78 scrape material from the end plates 66 of the adjacent vertebrae. The surgeon continues to remove bone material until the end plates achieve a desired surface contour to complement or mate with the implant 42, as shown in FIG. 10. The surgeon then removes the head portion 70 from the void 62 by applying digital pressure along the shaft 72, or by employing an instrument such as a slap hammer.

FIG. 10 illustrates one embodiment of a countersinking tool 88 that is adapted to shape the extradiscal lips 86 of adjacent vertebrae. A surgeon can use the countersinking tool in order to shape the extradiscal lips so that they more closely complement or mate with the tail flange 58 and prevent the implant 42 from being pushed into the intervertebral space 62.

The countersinking tool 88 includes a head portion 90 that extends from a distal end of a shaft 92. The head portion 90 and the shaft 92 can be formed integrally with one another, or the head portion 90 can be secured to the shaft 92 by any known means. The head portion and shaft are preferably rigid, and can be made of a metal, for example. In the illustrated embodiment, the head portion is shaped substantially the same as the implant 42, and includes a conical segment 94, a large cylindrical segment 96, a tapered segment 98, a small cylindrical segment 100 and a tail flange 102. Those of ordinary skill in the art will appreciate that the illustrated size and shape of the head portion 90 is merely an example, and in other embodiments a variety of shapes and sizes can be beneficial.

The conical segment 94, large cylindrical segment 96, tapered segment 98, and small cylindrical segment 100 each include a smooth outer surface. The smooth surfaces facilitate the entry of the head portion 90 into the intervertebral space 62, as described above with respect to the reaming tool 68. The tail flange 102 includes a roughened surface. This surface can, for example, be knurled or burred. The roughened surface is adapted to remove bone from the extradiscal lips 86 in order to reshape the lips so that they provide a surface that complements or mates with the contoured implant 42.

Figure 11:
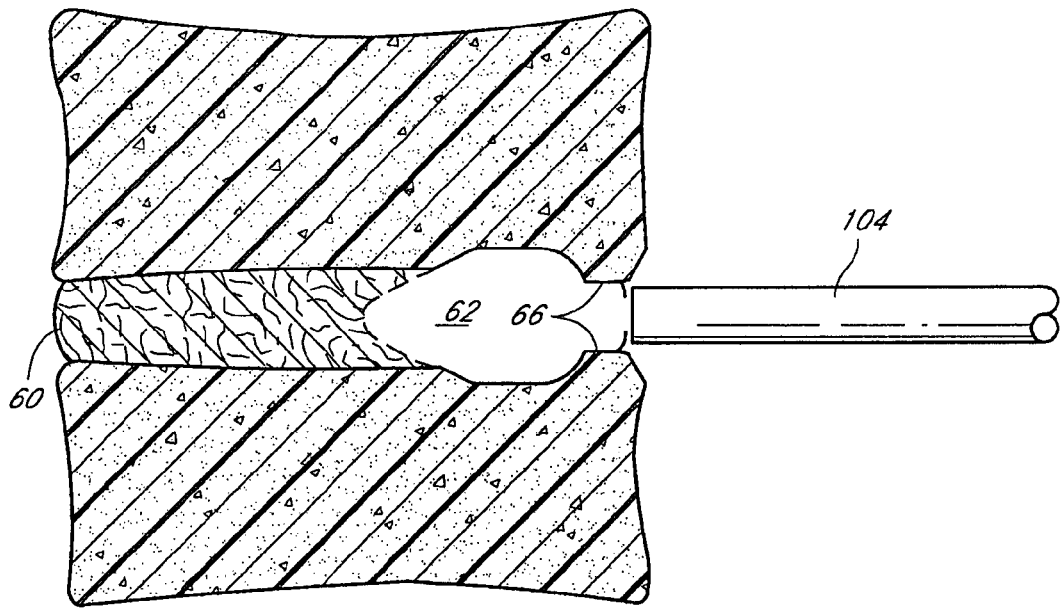
FIG. 11 is a right-side elevational view of the disc of FIG. 10 after the countersinking step, and a sizing tool that can be used during a procedure to implant the implant of FIG. 1.
Figure 12:
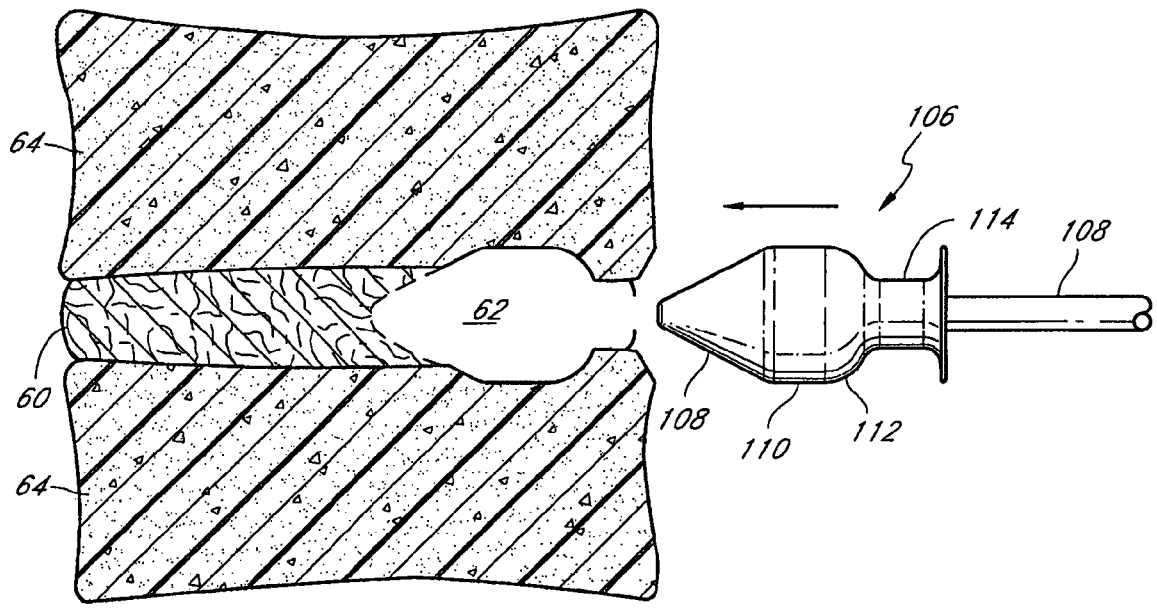
FIG. 12 is a right-side elevational view of the disc of FIG. 11 after the sizing step, and a trial implant that can be used during a procedure to implant the implant of FIG. 1.

In one embodiment of the method, the surgeon inserts the head portion 90 into the intervertebral space 62 in the same manner as described above with respect to the head portion 70. The head portion 90 preferably fits within the void 62 such that the roughened surface on the tail flange 102 abuts the extradiscal lips 86. To remove material from the lips 86, the surgeon rotates the shaft 92. As with the reaming tool 68, the surgeon can impart a rotational force to the shaft 92 by grasping the shaft with one's fingers, a gripping instrument, a manual rotation-generating tool, or a powered drill, for example. The rotating shaft 72 rotates the head portion so that the roughened surface on the tail flange 102 scrapes material from the lips 86. The surgeon continues to remove bone material until the end plates achieve a surface contour to complements or mates with the implant 42, as shown in FIG. 11. The surgeon then removes the head portion 90 from the void 62 in the same manner as described above with respect to the head portion 70.

In some embodiments it can also be desirable to omit the step of countersinking the extradiscal lips. In these cases the tail flange portion would abut the extradiscal lips, thus providing an effective barrier to prevent extrusion of material, in particular the nucleus pulposus, from the intervertebral disc space.

In certain embodiments, after the surgeon has shaped the vertebral end plates and extradiscal lips, he or she can use a sizing tool to measure the width of the opening between adjacent vertebral end plates 66. FIG. 11 illustrates one embodiment of a sizing tool 104. The tool comprises a cylindrical shaft of a known diameter. The surgeon can have several sizing tools of varying diameters close at hand during an implantation procedure. By attempting to insert sizing tools of increasing or decreasing diameters into the opening between adjacent vertebral end plates 66, the surgeon can measure the size of the opening. After measuring the distance between adjacent vertebral end plates 66, the surgeon will select the appropriate size of implant. He or she can begin with a trial implant, such as the implant 106 shown in FIG. 12.

Figure 13:
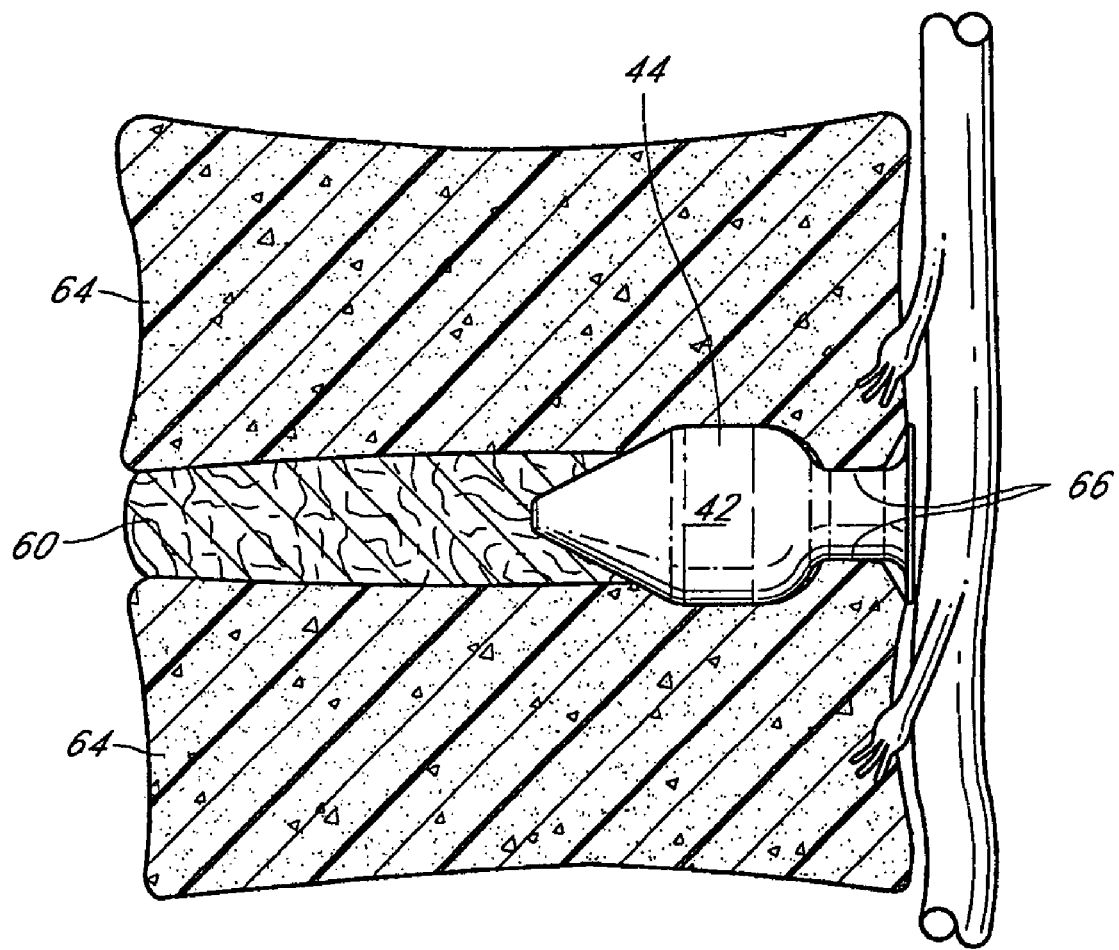
FIG. 13 is a right-side elevational view of the disc of FIG. 12 and the implant of FIG. 1, showing the implant implanted within the disc.

In the illustrated embodiment, the trial implant 106 is shaped exactly as the implant 42 of FIGS. 1-3, and is secured to the distal end of a shaft 108. The trial implant can be permanently or temporarily secured to the shaft. The surgeon can insert the trial implant 106 into the void 62 in the same manner as described above with respect to the head portions 70, 90. The smooth surface of the trial implant 106 facilitates its entry into the void 62. The conical portion 108 forces the vertebrae 64 apart as the surgeon advances the trial implant 108. Then, as the extradiscal lips pass over the large cylindrical segment 110 and reach the tapered segment 112, the vertebrae snap shut around the implant and the extradiscal lips come to rest around the small cylindrical segment 114. If the surgeon determines that the trial implant is the proper size to fit within the void, then he or she will withdraw the trial implant in the same manner as described above with respect to the head portions 70, 90. He or she will then select an implant that is the same size and shape as the trial implant 108, and insert the selected implant into the void 62, as shown in FIG. 13. The implant 42 can be temporarily secured to the distal end of a shaft (not shown), such that the insertion procedure is substantially the same as that described above with respect to the trial implant 108. If the implant is temporarily secured to the distal end of a shaft, it can engage the shaft through a threaded connection, bayonet mount, or other reversible fastener, for example. Once the implant is in place, the surgeon can then remove the shaft by unscrewing, or unfastening, from the implant.

The implant 42 advantageously stabilizes the region of the spine where it is implanted without substantially limiting the mobility of the region. Referring to FIGS. 3 and 13, it is seen that the conical segment 50, the large cylindrical segment 52, the tapered segment 54 and the small cylindrical segment 56 each abut and support the vertebral end plates 66, preventing the vertebrae 64 from moving closer to one another. Further, interengagement of the shaped end plates 66 and the tapered segment 54 resists any forces tending to push the implant 42 out of the intervertebral space, while interengagement of the tail flange 58 and the shaped extradiscal lips 86 resists any forces tending to push the implant 42 deeper into the intervertebral space. The border of the defect in the disc annulus (not visible in FIG. 13) comes to rest on the small cylindrical segment 56 and the tail flange 58, thus preventing any of nucleus pulposus from being squeezed out of the defect.

In some embodiments, the implantation procedure described above could be performed using a guard device that would not only prevent surrounding tissue from interfering with the procedure, but also protect the surrounding tissue from damage. For example, a tubular guard (not shown) can be employed around the implantation site. The guard would prevent surrounding tissue from covering the implantation site, and prevent the implantation instruments from contacting the surrounding tissue.

In certain embodiments of the present methods, the spacing between adjacent vertebrae is preferably maintained. Thus, the spacing between adjacent vertebrae after one of the present implants has been inserted therebetween is preferably approximately the same as the spacing that existed between those same vertebrae prior to the implantation procedure. In such a method it is unnecessary for the implanting physician to distract the vertebrae prior to introducing the implant. As described above, the increasing size of the conical segment and the large cylindrical segment of the implant temporarily distracts the vertebrae as it passes between the discal lips thereof, after which the vertebrae snap shut around the implant. In certain other embodiments of the present methods, however, it can be advantageous to increase the spacing of the adjacent vertebrae through the implantation procedure, so that the spacing between the adjacent vertebrae after the implant has been inserted therebetween is greater than the spacing that existed between those same vertebrae prior to the implantation procedure. In such embodiments, the implanting physician can deflect, displace, or manipulate the adjacent vertebrae prior to implanting the implant in order to achieve the desired spacing.

Figure 14:
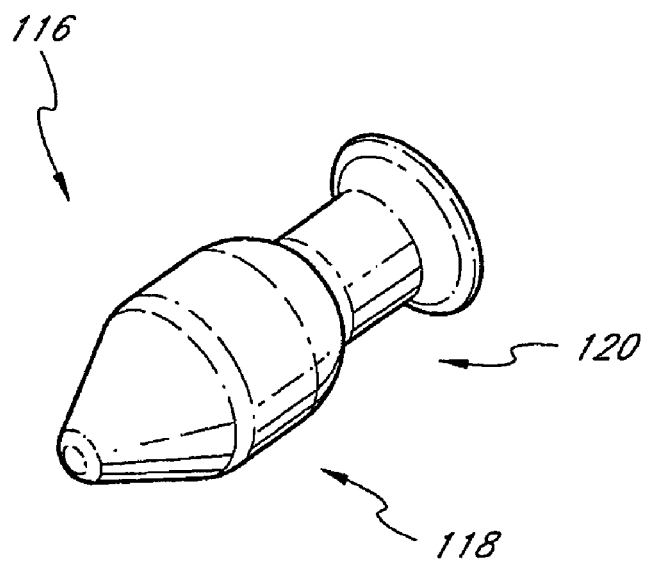
FIG. 14 is a front perspective view of another embodiment of the present spinal implants.
Figures 15, 16:
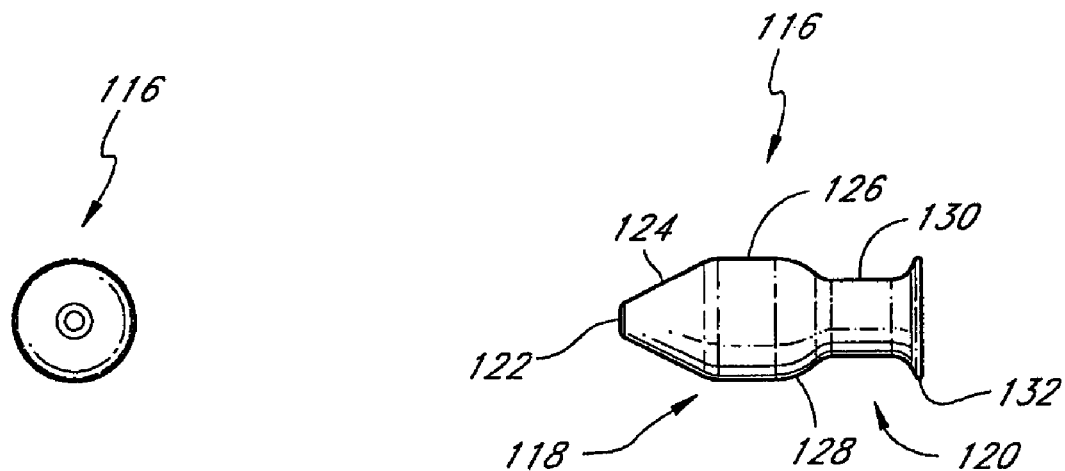
FIG. 15 is a front elevational view of the spinal implant of FIG. 14.
FIG. 16 is a right-side elevational view of the spinal implant of FIG. 14.

FIGS. 14-22 illustrate alternative embodiments of the present spinal implants. These alternative embodiments are adapted for use in spinal discs where the patient's anatomy is better suited to an implant having a different size and/or shape. For example, FIGS. 14-16 illustrate a spinal implant 116 having an enlarged head portion 118 and a relatively narrow tail portion 120 (FIG. 16). As in the implant 42 of FIGS. 1-3, the head portion 118 of the implant 116 of FIGS. 14-16 includes a substantially flat nose 122, a conical segment 124, a large cylindrical segment 126 and a tapered segment 128. The tail portion 120 includes a small cylindrical segment 130 and a tail flange 132. In comparing the embodiment of FIGS. 1-3 to the embodiment of FIGS. 14-16, the conical segment 50 is longer than the conical segment 124, and the large cylindrical segment 52 is wider in diameter than the large cylindrical segment 126. The tail flange 58 is also somewhat wider in diameter than the tail flange 132. Thus, the implant 116 of FIGS. 14-16 is adapted for implantation in an intervertebral disc having a relatively small diameter, or where it is advantageous for the implant 116 to penetrate only a relatively short distance into the disc.

Figure 17:
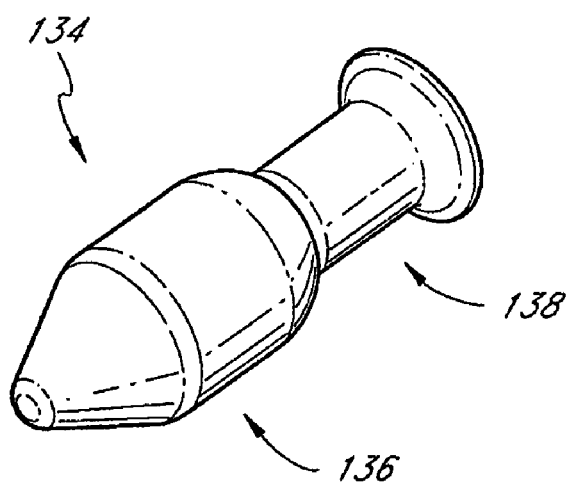
FIG. 17 is a front perspective view of another embodiment of the present spinal implants.
Figures 18, 19:
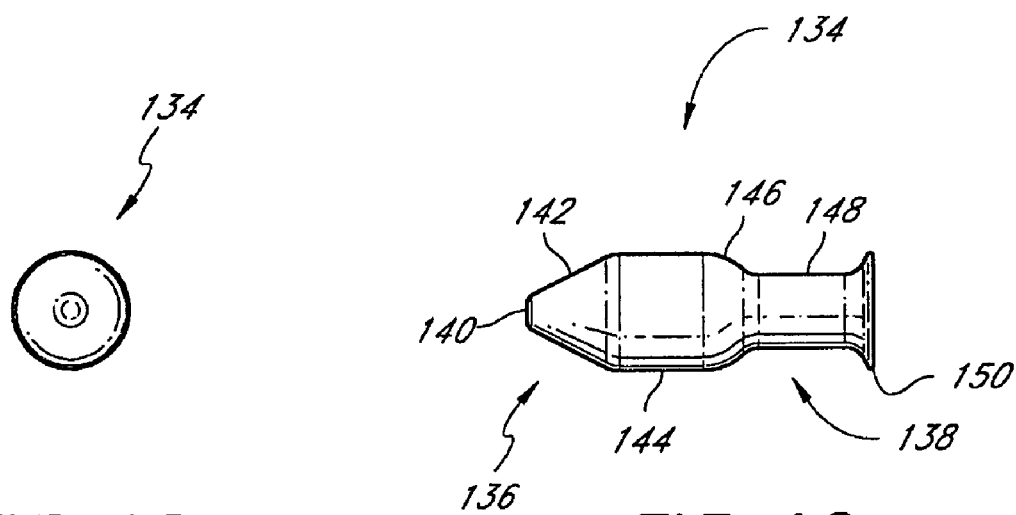
FIG. 18 is a front elevational view of the spinal implant of FIG. 17.
FIG. 19 is a right-side elevational view of the spinal implant of FIG. 17.

FIGS. 17-19 illustrate a spinal implant 134 having an enlarged head portion 136 and a relatively narrow tail portion 138 (FIG. 19). Cross-sections taken perpendicularly to a longitudinal axis of the implant are all substantially circular; however, the area of a given cross-section varies along the longitudinal axis. As in the implants described above (and as with all implants described herein and encompassed by the claims below), the cross-sectional shape of the implant 134 need not be circular, and could be, for example, elliptical, rectilinear, triangular, or oval. Further, the cross-sectional shapes of the implants described herein can vary along the longitudinal axis.

The head portion 136 includes a substantially flat nose 140 at a first end of a conical segment 142. The conical segment increases in height and cross-sectional area at a substantially constant rate from the nose to a first end of a large cylindrical segment 144. The large cylindrical segment extends at a constant height and cross-sectional area from the conical segment to a first end of a tapered segment 146. The tapered segment decreases in height and cross-sectional area at an increasing rate from the large cylindrical segment to a first end of a small cylindrical segment 148. The small cylindrical segment is substantially smaller in height than the large cylindrical segment, and extends from the tapered segment to a tail flange 150. The tail flange flares outwardly from a minimum height and cross-sectional area at a second end of the small cylindrical segment to a maximum height and cross-sectional area at a second end of the implant 134. The maximum height of the tail flange can be approximately equal to that of the large cylindrical segment.

A comparison between the implant 116 of FIGS. 14-16 and the implant 134 of FIGS. 17-19 reveals that the implant 134 of FIGS. 17-19 has a longer large cylindrical segment 144 and a longer small cylindrical segment 148. The remaining segments in the implant 134 are substantially similar to their counterparts in the implant 116. The implant 134 of FIGS. 17-19 is thus adapted for implantation in an intervertebral disc where it is advantageous for the implant 134 to penetrate a greater distance into the disc as compared to the implant 116 of FIGS. 14-16.

Figure 20:
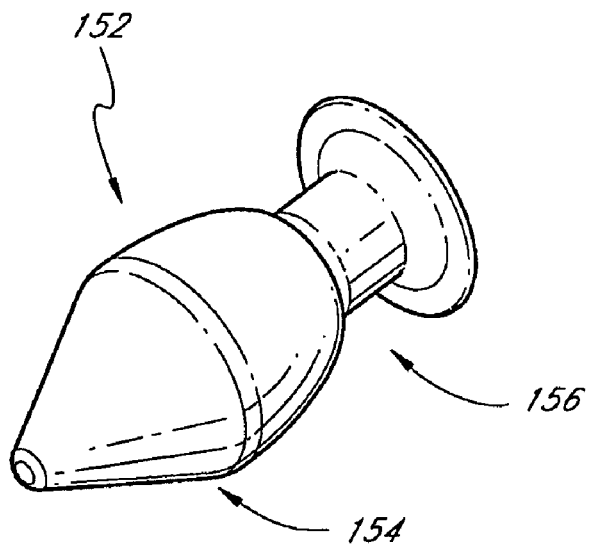
FIG. 20 is a front perspective view of another embodiment of the present spinal implants.
Figures 21, 22:
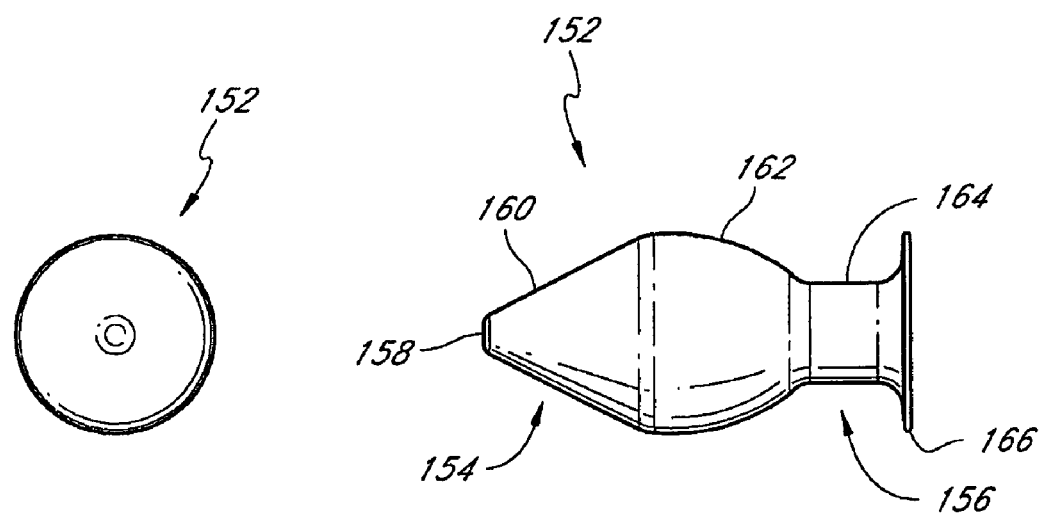
FIG. 21 is a front elevational view of the spinal implant of FIG. 20.
FIG. 22 is a right-side elevational view of the spinal implant of FIG. 20.

FIGS. 20-22 illustrate a spinal implant 152 having a shape that is similar to the implant 42 of FIGS. 1-3. The implant 152 includes an enlarged head portion 154 and a relatively narrow tail portion 156 (FIG. 22). As in the implant 42 of FIGS. 1-3, the head portion 154 of the implant 152 of FIGS. 20-22 includes a substantially flat nose 158, a conical segment 160 and a tapered segment 162. However, the implant 152 does not include a large cylindrical segment. Instead, the conical segment directly adjoins the tapered segment, and the tapered segment tapers at a more gradual rate as compared to the tapered segment 54 of the implant 42 of FIGS. 1-3. The head portion 154 achieves a maximum height at the junction between the conical segment 160 and the tapered segment 162. This area of maximum height is adapted to provide stability to the adjacent vertebrae. As with the implant 42 of FIGS. 1-3, the tail portion 156 of the implant 152 of FIGS. 20-22 includes a small cylindrical segment 164 and a tail flange 166.

Those of skill in the art will appreciate that the relative dimensions shown in the figures are not limiting. For example, in FIG. 13 the implant 42 is illustrated as having certain dimensions relative to the dimensions of the vertebrae 64. In fact, the size of the implant relative to the vertebrae will be chosen based upon a variety of factors, including the patient's anatomy and the size of the annular defect to be repaired. In certain applications the implant can be significantly smaller relative to the vertebrae, and can extend significantly less than halfway toward a vertical centerline of the intervertebral disc. In certain other applications the implant can be significantly larger relative to the vertebrae, and can extend almost all the way across the intervertebral disc.

Figure 23:
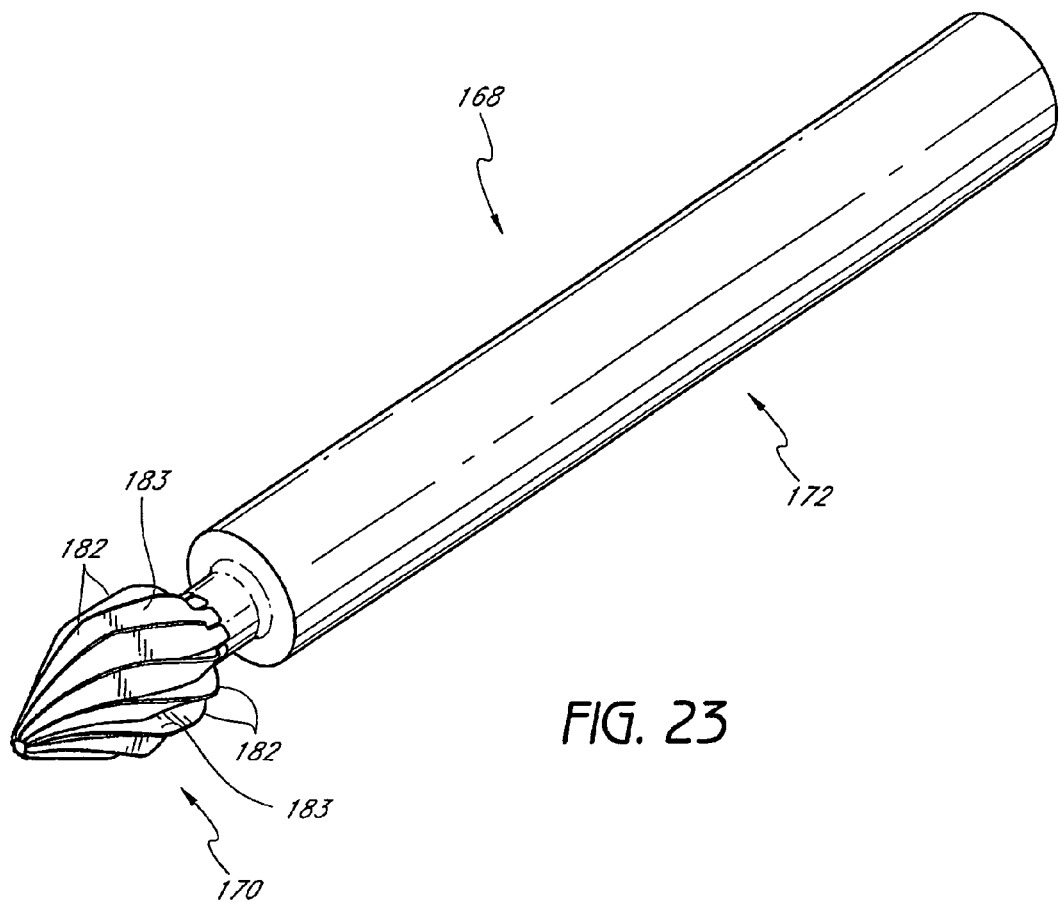
FIG. 23 is a front perspective view of another embodiment of a reaming tool that can be used during a procedure to implant the present implants.
Figure 24:
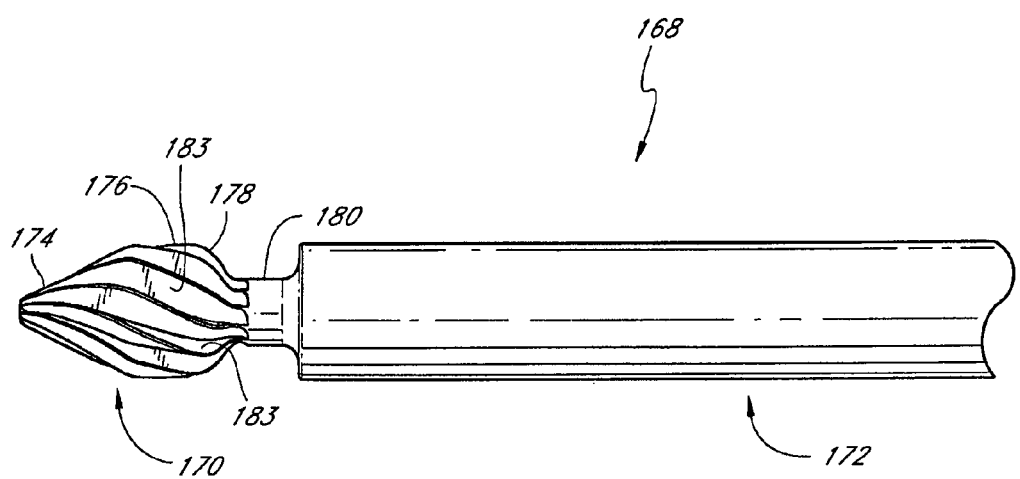
FIG. 24 is a right-side elevational view of the reaming tool of FIG. 23.

FIGS. 23 and 24 illustrate an alternative reaming tool 168 that can be used to shape the end plates of adjacent vertebrae. The reaming tool 168, which is similar to the reaming tool 68 described above and pictured in FIG. 9, includes a head portion 170 that extends from a distal end of a shaft 172. The head portion 170 and the shaft 172 can be formed integrally with one another, or the head portion 170 can be secured to the shaft 172 by any known means. The head portion 170 and shaft 172 are preferably rigid, and can be made of a metal, for example. In the illustrated embodiment, the head portion 170 is shaped similarly to the implant 42, and includes a conical segment 174, a large cylindrical segment 176, a tapered segment 178 and a small cylindrical segment 180 (FIG. 24). Those of ordinary skill in the art will appreciate that the illustrated size and shape of the head portion 170 is merely an example. However, it is advantageous for the head portion 170 to be of similar size and shape to the implant that will ultimately be implanted in the intervertebral space (whether that size and shape is the same as or different from the implant 42 of FIGS. 1-3). In the illustrated embodiment, the shaft 172 has a greater width relative to the head portion 170 as compared to the reaming tool 68 described above, thereby making the reaming tool 168 easier to grip.

A plurality of curved blades 182 (FIG. 23) extend along the surfaces of the conical segment 174, the large cylindrical segment 176, the tapered segment 178 and the small cylindrical segment 180, giving the head portion 170 a scalloped surface. The blades 182 extend in a substantially helical pattern along a longitudinal axis of the head portion 170. Each pair of adjacent blades 182 is separated by a cavity 183. The blades 182 are adapted to remove bone from the vertebral end plates 66 in order to reshape the end plates so that they provide a surface that is complementary to the contoured implant 42. Operation of the reaming tool 168 is substantially identical to operation of the reaming tool 68 described above. The blades 182 scrape bone material away as the reaming tool 168 is rotated, and the cavities 183 provide a volume to entrain removed bone material.

In some embodiments, the blades 182 are not curved but instead are substantially straight. The blades 182 can be oriented substantially parallel to the longitudinal axis. The blades 182 can curve in the radial direction to follow the outer surface of the head 170 of the reaming tool 168.

In certain embodiments, rather than having curved blades, the reaming tool 172 might be fashioned to provide a head portion 170 adapted to cut threads in the vertebral surfaces adjacent to the site of repair, analogous to a "tap" used in the mechanical arts to thread holes to receive bolts or screws. Providing a reaming tool with the ability to thread a repair site would provide a thread pattern that would substantially fit the pitch and depth of the threads included in an embodiment of the present spinal implant, for example that illustrated in FIG. 32A.

Figure 25:
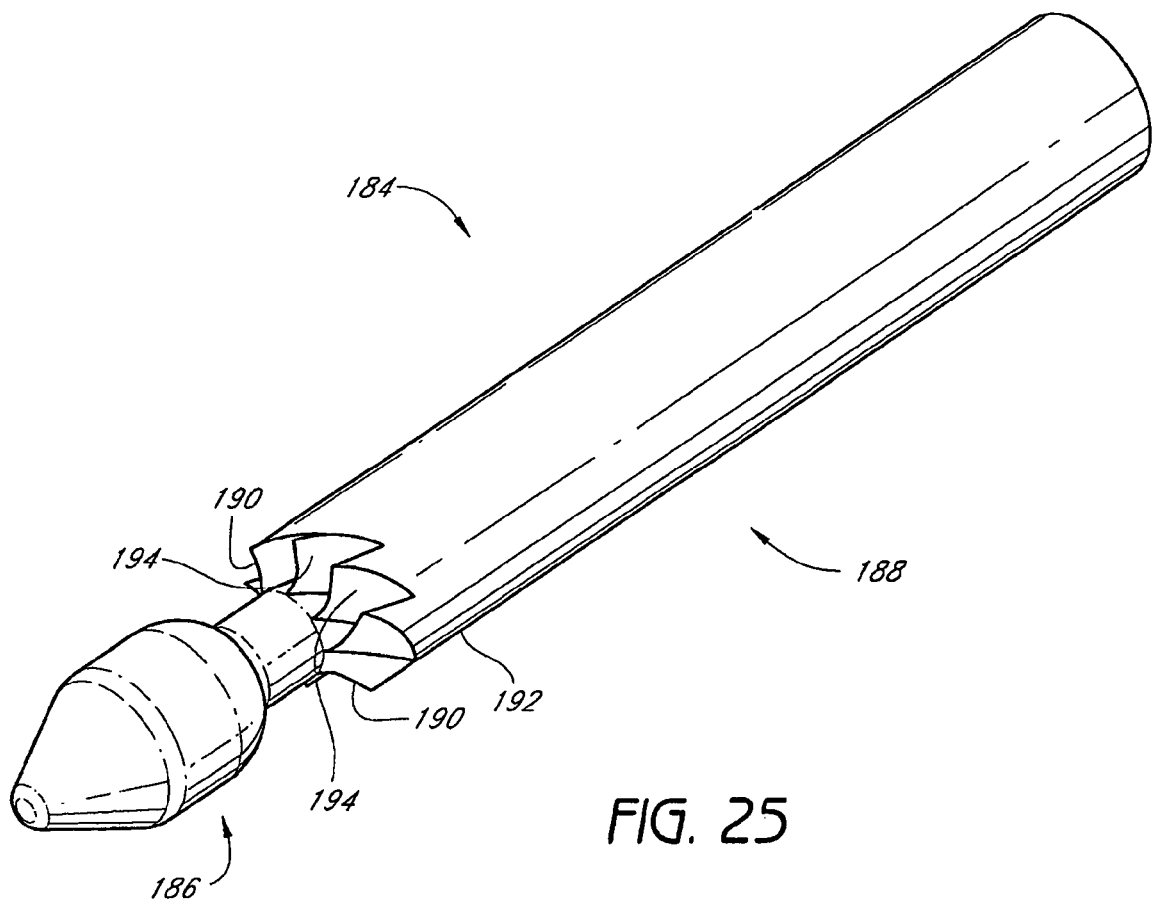
FIG. 25 is a front perspective view of another embodiment of a countersinking tool that can be used during a procedure to implant the present implants.
Figure 26:
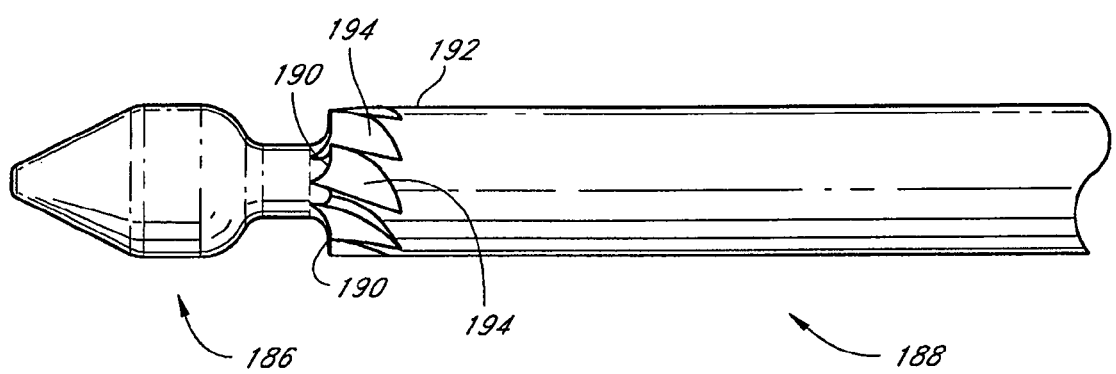
FIG. 26 is a right-side elevational view of the countersinking tool of FIG. 25.

FIGS. 25 and 26 illustrate an alternative countersinking tool 184 that can be used to shape the extradiscal lips of adjacent vertebrae. The countersinking tool 184, which is similar to the countersinking tool 88 described above and pictured in FIG. 10, includes a head portion 186 that extends from a distal end of a shaft 188. The head portion 186 and the shaft 188 can be formed integrally with one another, or the head portion 186 can be secured to the shaft 188 by any known means. The head portion 186 and shaft 188 are preferably rigid, and can be made of a metal, for example. In the illustrated embodiment, the head portion 186 is shaped similarly to the implant 42. Those of ordinary skill in the art will appreciate that the illustrated size and shape of the head portion 186 is merely an example. However, it is advantageous for the head portion 186 to be of similar size and shape to the implant that will ultimately be implanted in the intervertebral space (whether that size and shape is the same as or different from the implant 42 of FIGS. 1-3). In the illustrated embodiment, the shaft 188 has a greater width relative to the head portion 186 as compared to the countersinking tool 88 described above, thereby making the countersinking tool 184 easier to grip.

A plurality of curved blades 190 extend around a distal end 192 of the shaft 188, adjacent the head portion 186. An edge of each blade 190 faces the head portion 186, and each pair of adjacent blades 190 is separated by a wedge-shaped cavity 194. The blades 190 are adapted to remove bone from the extradiscal lips of adjacent vertebrae in order to reshape the vertebrae so that they provide a surface that is complementary to the contoured implant 42. Operation of the countersinking tool 184 is substantially identical to operation of the countersinking tool 88 described above. The blades 190 scrape bone material away as the countersinking tool 184 is rotated, and the cavities 194 provide a volume to entrain removed bone material.

In certain embodiments the reaming tool can further comprise a stop to prevent the tool from penetrating into the intervertebral disc further than a desired distance. In some embodiments the stop can comprise a flange on the shaft of the reaming tool that abuts the vertebrae when the tool has been inserted the desired distance.

Figure 27:
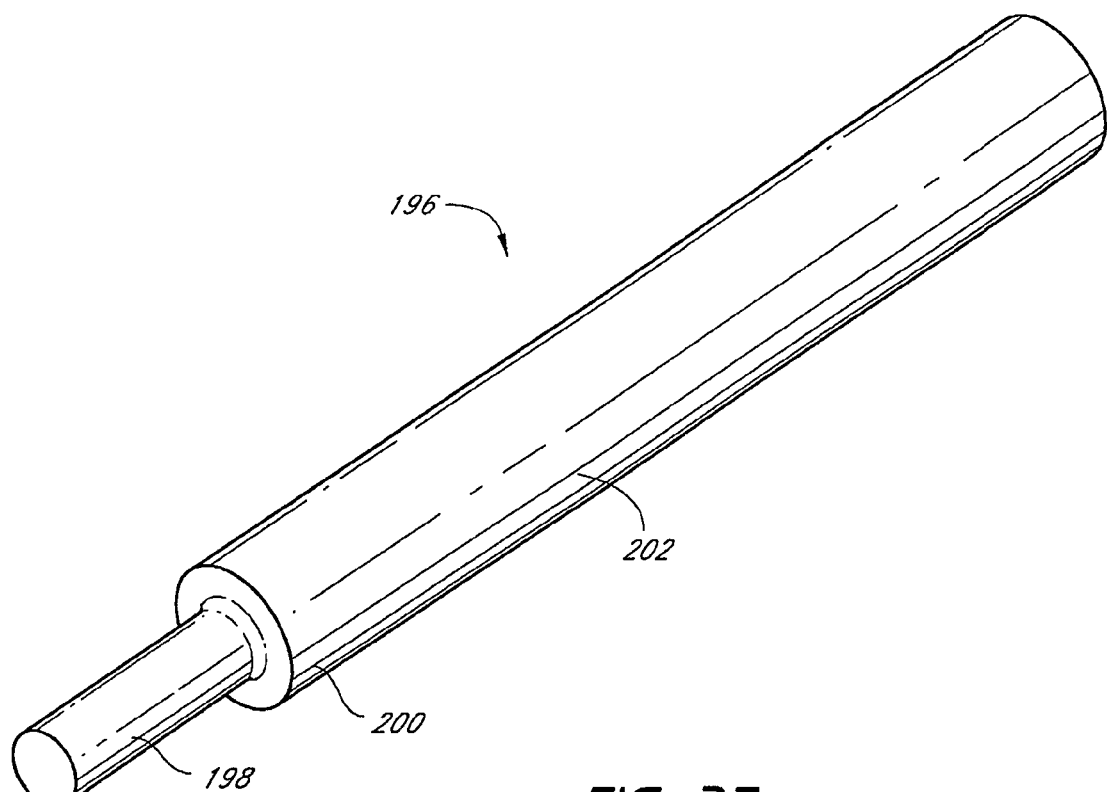
FIG. 27 is a front perspective view of another embodiment of a sizing tool that can be used during a procedure to implant the present implants.
Figure 28:
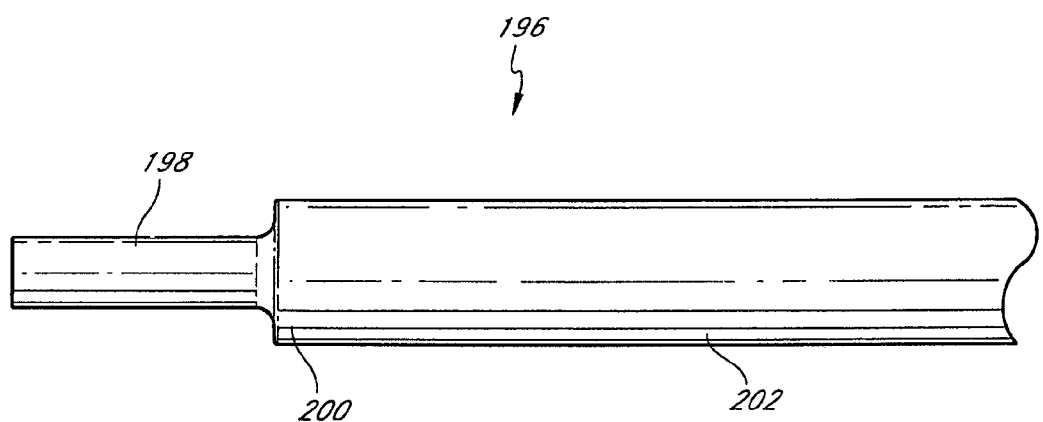
FIG. 28 is a right-side elevational view of the sizing tool of FIG. 27.

FIGS. 27 and 28 illustrate another embodiment of a sizing tool 196. The tool comprises a cylindrical shaft 198 of a known diameter that extends from a distal end 200 of a handle portion 202. Operation of the sizing tool 196 is substantially identical to operation of the sizing tool 104 described above. However, the sizing tool 196 of FIGS. 27 and 28 advantageously has a handle portion 202 that is wider than the cylindrical shaft 198, thereby making the sizing tool 196 easier to grip.

Figure 29:
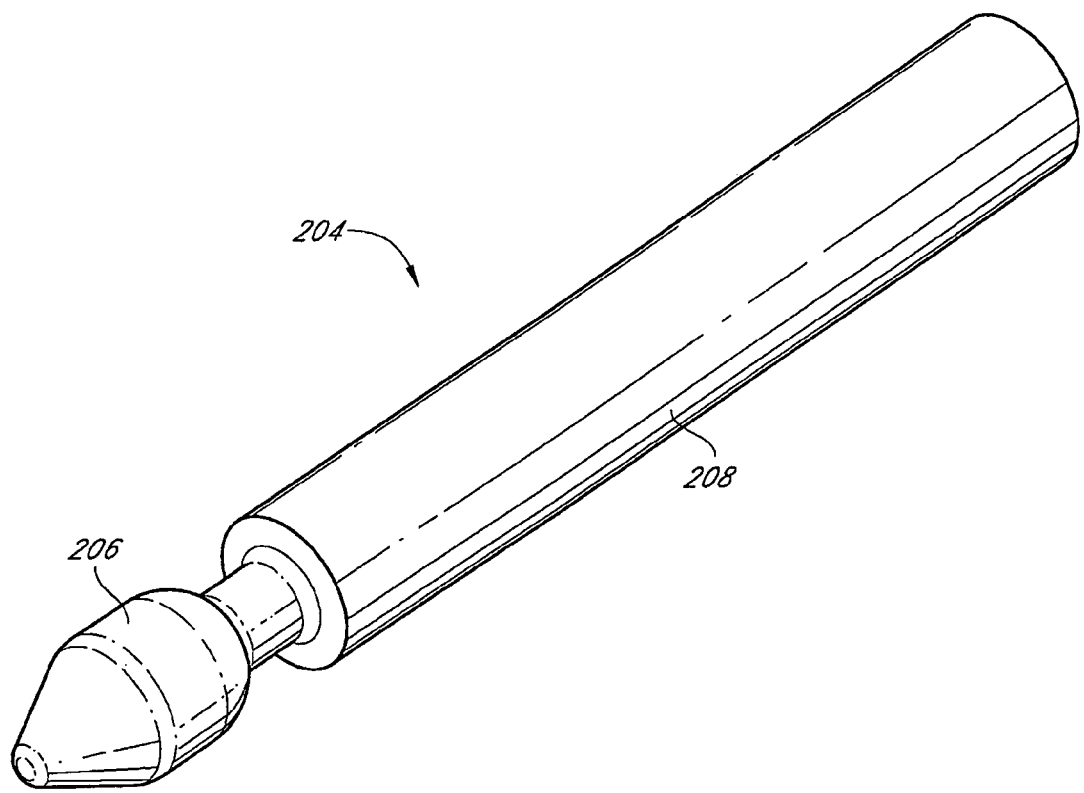
FIG. 29 is a front perspective view of another embodiment of a trial implant that can be used during a procedure to implant the present implants.
Figure 30:
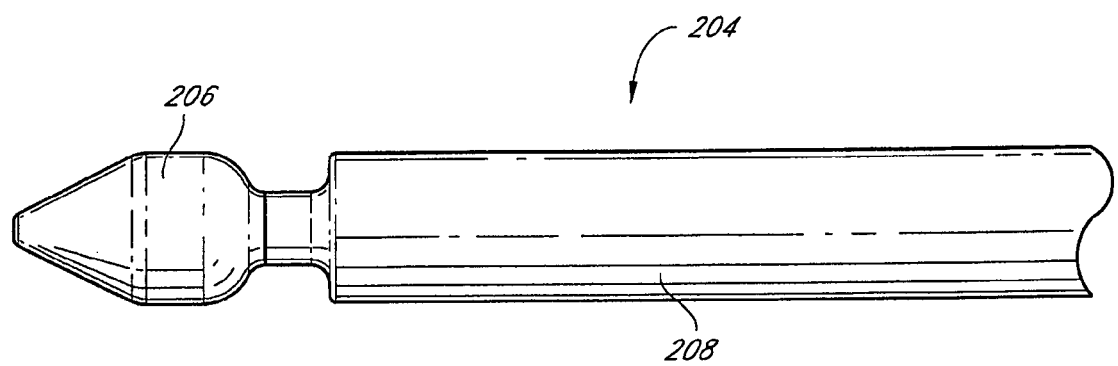
FIG. 30 is a right-side elevational view of the trial implant of FIG. 29.

FIGS. 29 and 30 illustrate another embodiment of a trial implant 204. The trial implant 204, which comprises an implant portion 206 and a handle portion 208, is similar to the trial implant 106 described above. However, the trial implant 204 of FIGS. 29 and 30 advantageously has a wider handle portion 204, thereby making the trial implant 204 easier to grip.

In addition to the embodiments described above, a number of variations in the structure, shape or composition of the spinal implant are also possible and are intended to fall within the scope of the present invention.

Figure 31A:
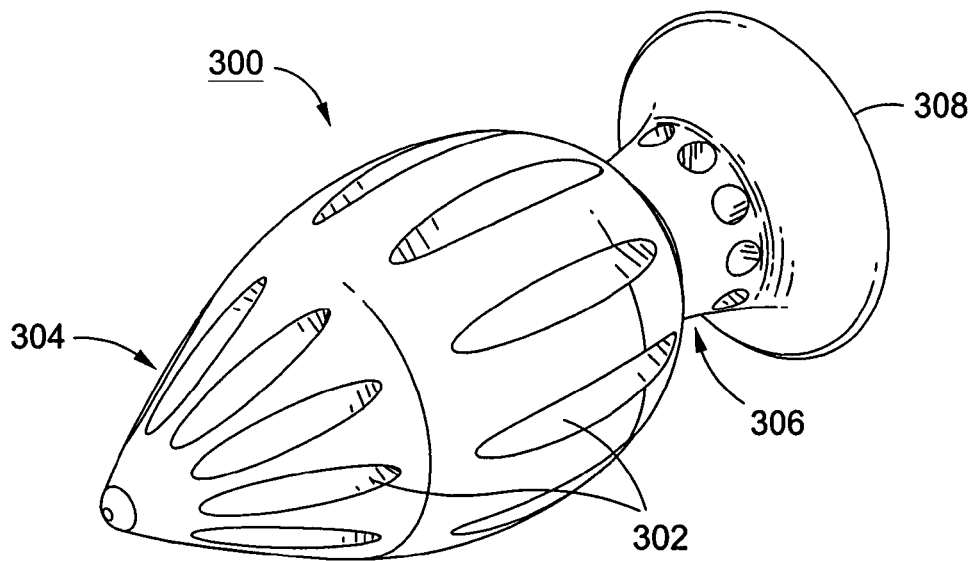
FIG. 31 illustrates a front perspective view of a hollow spinal implant with bone compaction holes (A), and the device implanted within the disc (B).
Figure 31B:
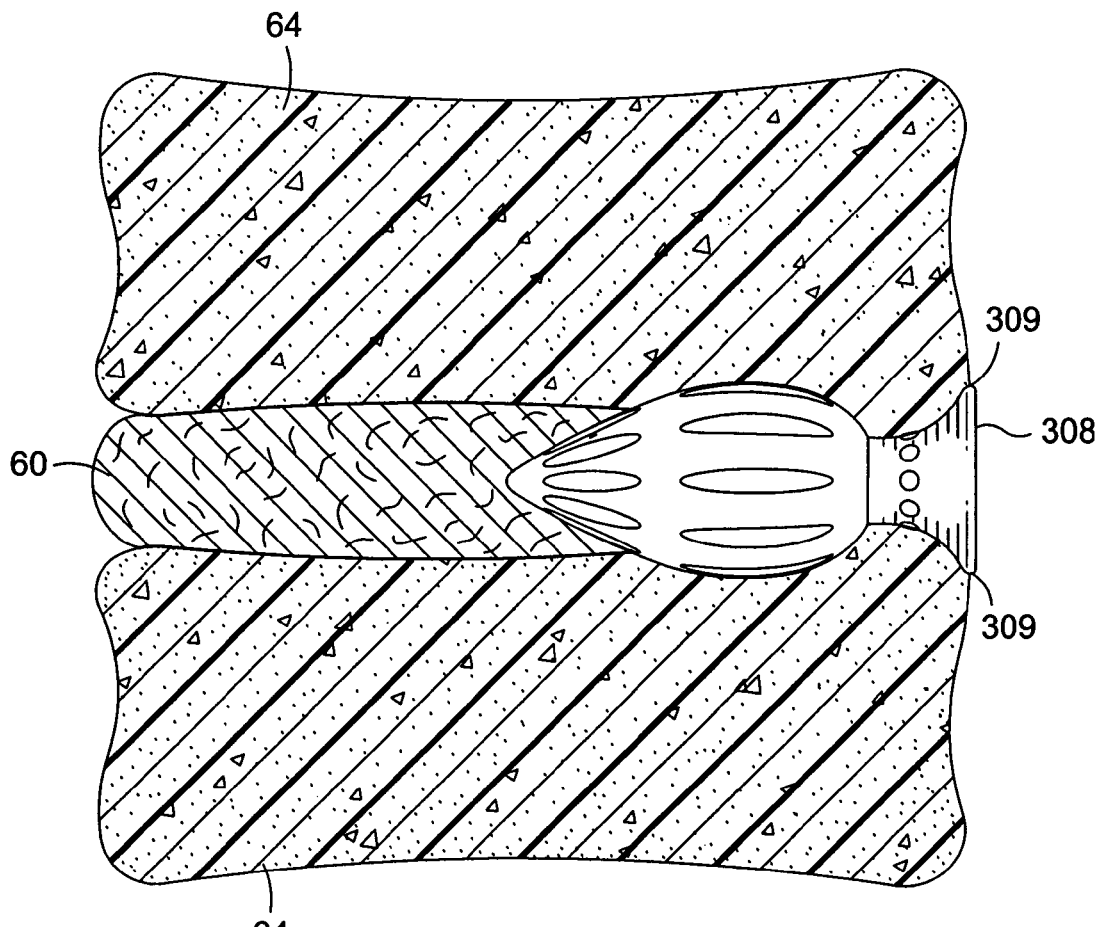

For example, in certain embodiments, one of which is depicted in FIG. 31A, the spinal implant 300 can be relatively hollow and can further comprise bone graft compaction holes 302. Either the head portion 304 and/or tail portion 306 can be hollow, and either or both can include holes as desired. The compaction holes 302 will permit spring back of vertebral bone into the implant, thus further securing the implant when it is placed in the intervertebral space between two adjacent vertebrae 64. Compaction holes 302 can also permit the ingrowth of adjacent bone or other connective tissue, thus further stabilizing the implant. As depicted in FIG. 35B, the tail flange 308 abuts the extradiscal lips 309 of adjacent vertebrae operative to limit or prevent extrusion of material such as nucleus pulposus from the intervertebral disc 60 when the barrier portion is positioned such that it contacts an outer surface of the annulus fibrosis and spans the width of the annular defect.

Figure 32A:
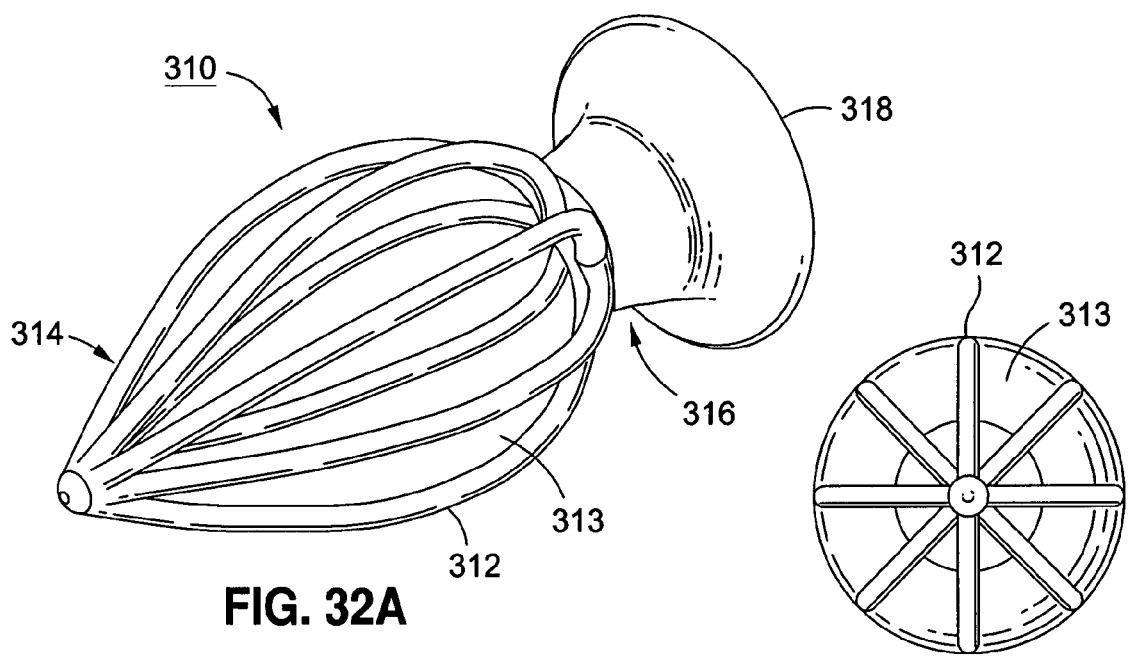
FIG. 32 illustrates a front perspective view of a hollow splined spinal implant with (A), the device implanted within the disc (B), and a front view of the implant (C).
Figure 32C:
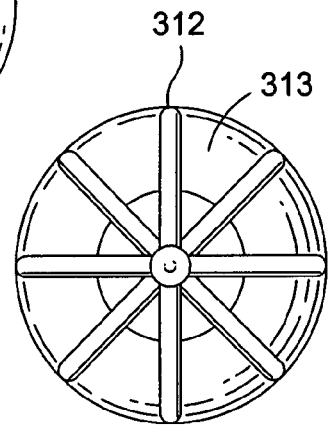
Figure 32B:
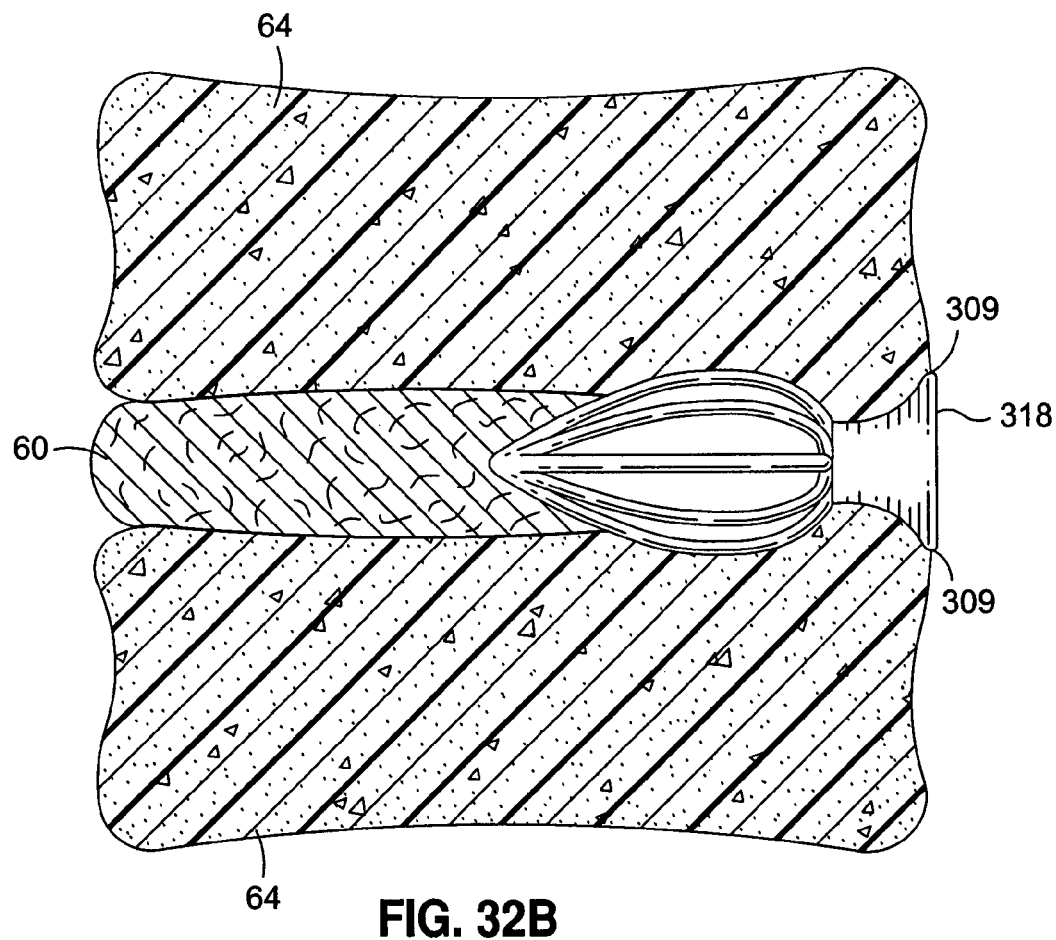

In some embodiments, one of which is depicted in FIG. 32A, the spinal implant 310 can include splines. The splines 312 can be spaced apart in a wire or basket-like configuration, the spaces between splines 314 providing access to the interior of the implant such that the implant is effectively hollow. In some embodiments, the material used to fashion the splines can be chosen to mimic the natural deformability of the annulus, while retaining sufficient rigidity to maintain a proper distance between the adjacent vertebrae 64, consistent with the spacer function provided by the head portion of the implant. The device can be constructed such that the head 314 alone is splined, the tail 318 alone is splined, or both the head and tail are splined. The tail flange 318 abuts the extradiscal lips 319 of adjacent vertebrae, operative to limit or prevent extrusion of material from the intervertebral disc 60 when the barrier portion is positioned such that it contacts an outer surface of the annulus fibrosis and spans the width of the annular defect. In a hollow implant, the splines can deform elastically, thus providing a spring action in the direction of one or more axes.

In some embodiments, a splined implant can have a solid surface. For example, an implant 320 can be solid with a spline 322 and groove 323 pattern forming the surface of the implant as depicted in FIG. 33A. Splined implants provide an advantage in that they will tend to resist rotation, which will serve to better secure the implant at the repair site as shown in FIG. 33B. As with other embodiments the tail flange 328 abuts extradiscal lips 309 of adjacent vertebrae providing a barrier. Again, splines can be included on the head portion 324, the tail portion 326, or both the head and tail portion. The splines can be substantially aligned with the longitudinal axis of the implant, or alternatively, can have a rotational pitch imparted on them. Where the splines have a rotational pitch imparted on them, placement of the implant can be accomplished by a combined pushing and twisting motion.

Figure 34A:
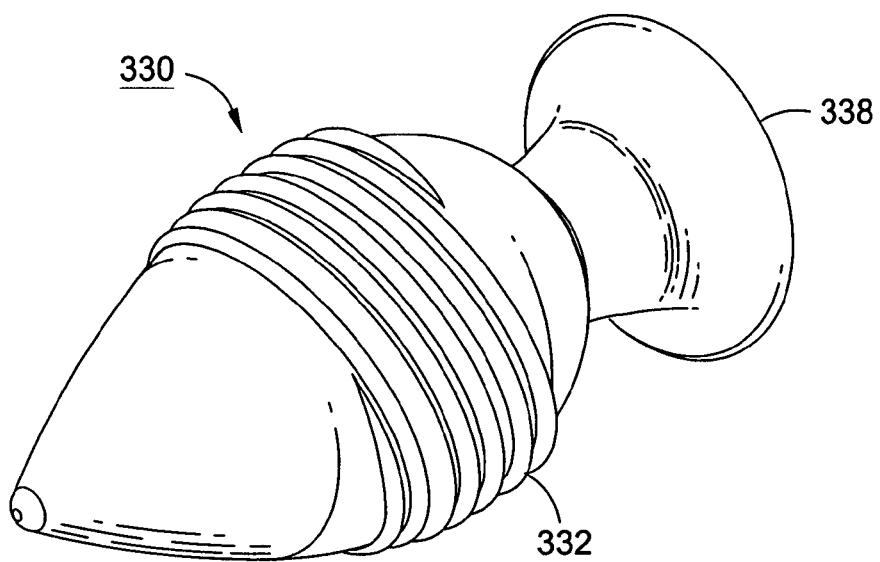
FIG. 34 illustrates a front perspective view of a threaded spinal implant with (A), and the device implanted within the disc (B).
Figure 34B:
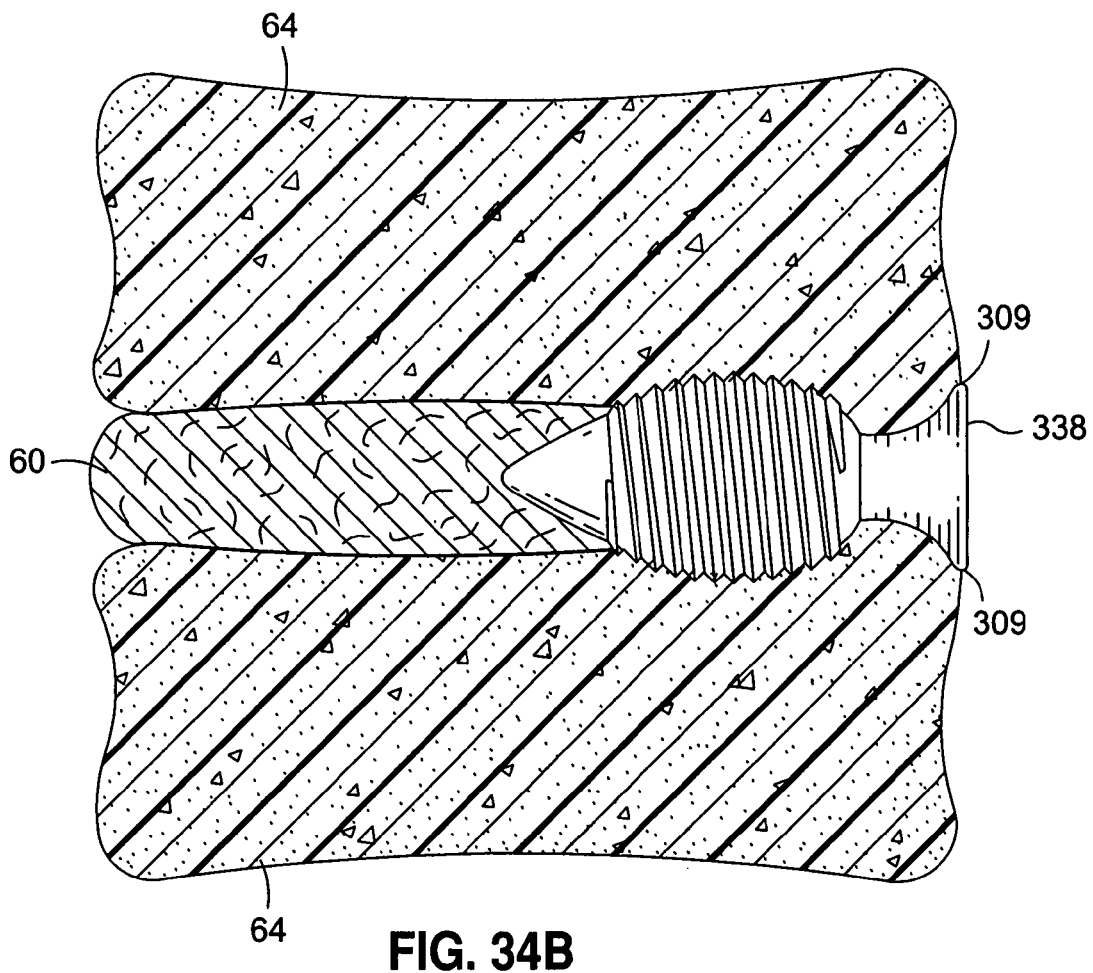

In some embodiments, the implant 330 can include a spiral "barb" 332 analogous to a screw thread, one of which is illustrated in FIG. 34A. In a spiral barb embodiment, placement and securing of the implant might also involve turning the implant such that the thread engages adjacent vertebrae 64 permitting the implant to be threaded into the intervertebral space. If desired the surface of adjacent vertebrae could be prepared by cutting a thread of substantially the same pitch as that on the implant head using a thread cutting tool, much like the typical method of tapping a hole in order to provide a means to engage a bolt as is well known in the mechanical arts. In this way, the implant could be more easily threaded into place, and a more secure fit would be obtained. Threading the implant into place further allows the tail flange 338 to be brought up snugly against the extradiscal lips 309 thus improving the barrier function of the implant, as is shown in FIG. 34B.

Figure 35A:
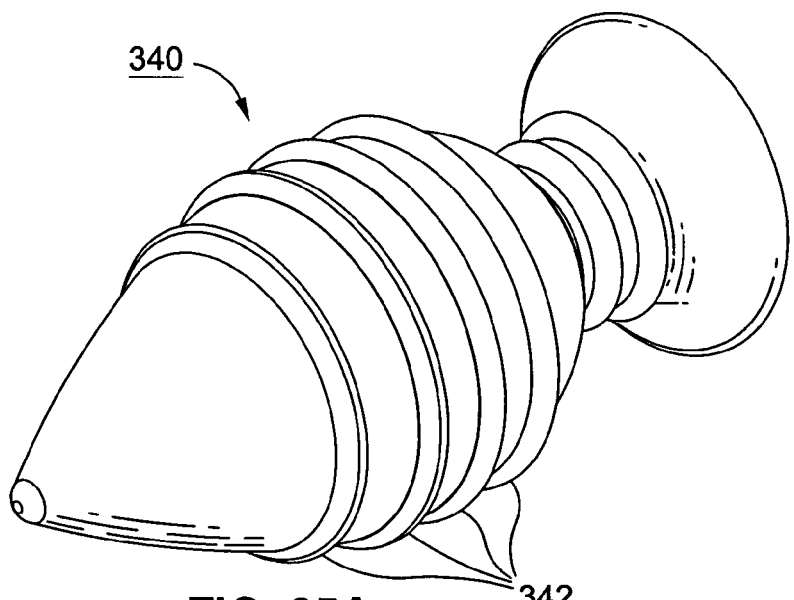
FIG. 35 illustrates a front perspective view of a spinal implant with circumferential rings (A), and the device implanted within the disc (B).
Figure 35B:
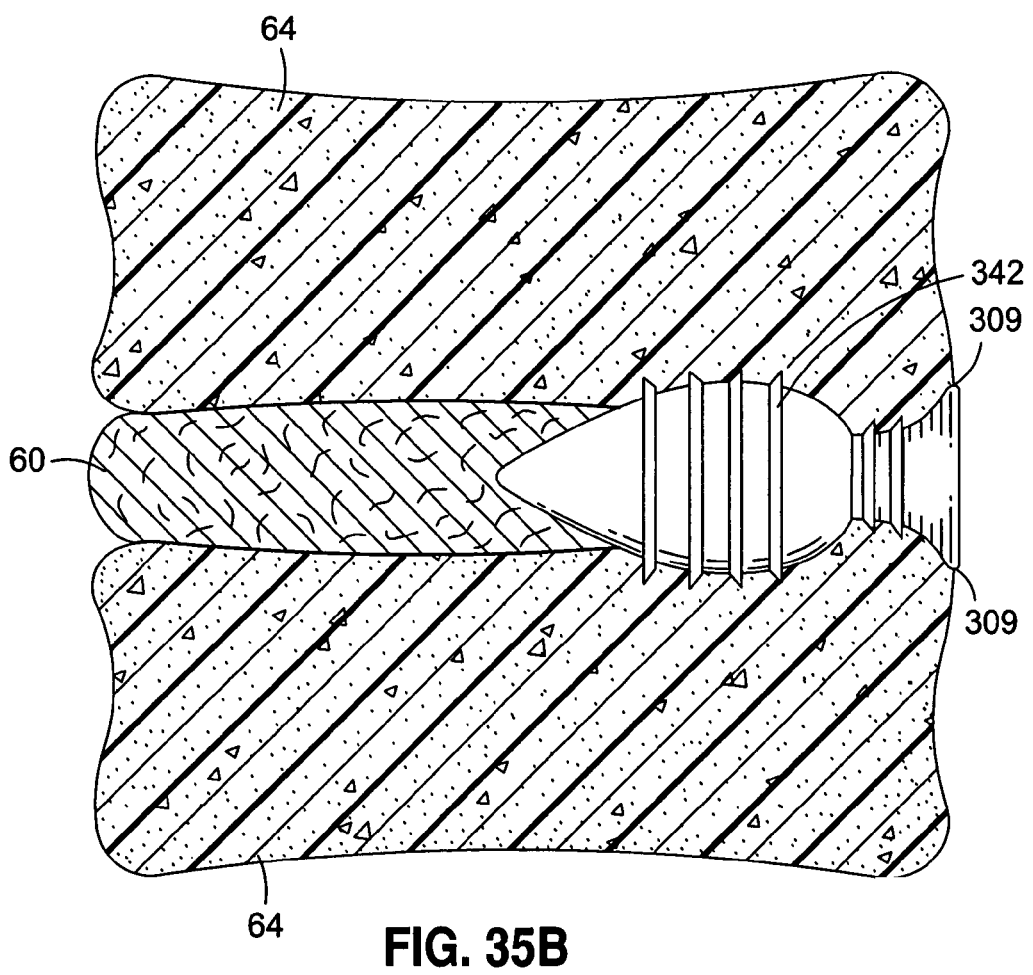

In some embodiments of the spinal implant 340, a plurality of substantially concentric barbs 342, one of which is shown in FIG. 35A, might be included. The orientation of the barbed ends could be biased either towards the front or rear of the spinal implant. Biasing of the barbs would provide an advantage in that barbs would better resist movement of the implant either in or out of the site of implantation, as is shown in FIG. 35B. Barbs can be provided either on the head portion, the barrier portion or both as desired. The number of barbs is not limiting to the invention and one or more barbs can be effective.

Figure 36A:
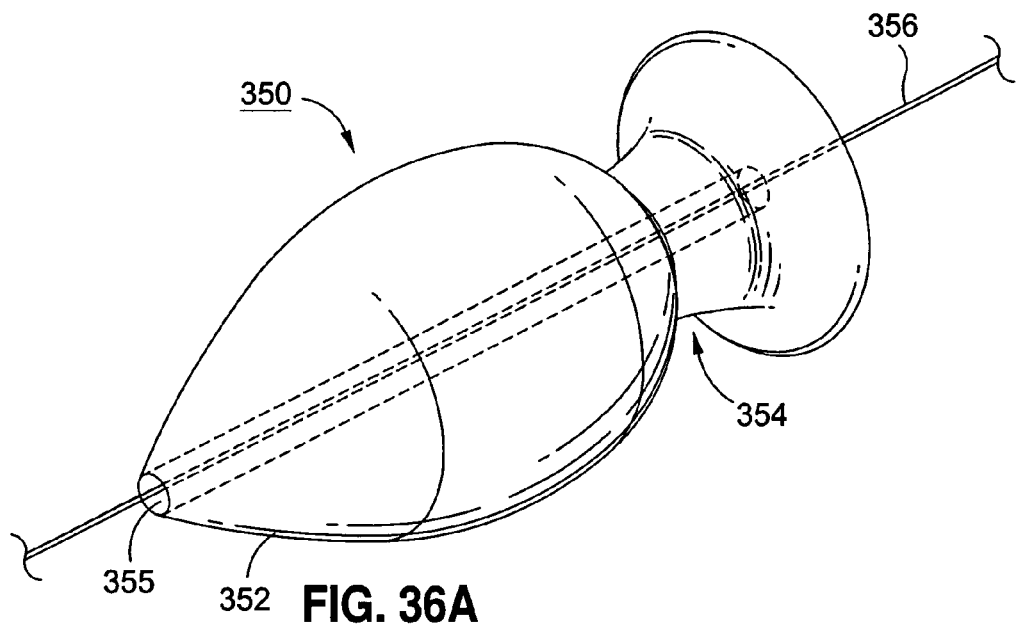
FIG. 36 illustrates a front perspective view of a spinal implant a centrally located hole for placement of the implant with a guide wire (A), and the device implanted within the disc (B).
Figure 36B:
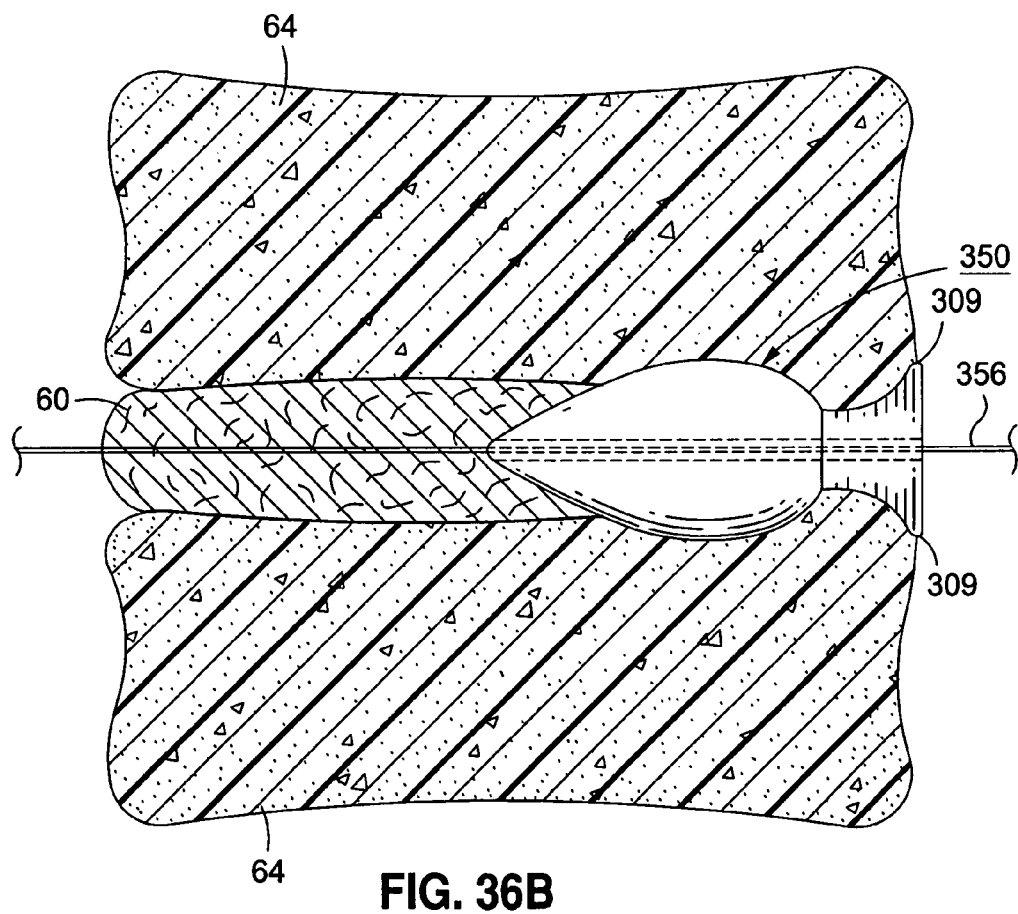

In some embodiments, one of which is illustrated in FIG. 36 the implant 350 comprises a head portion 352 and tail portion 354 with a lumen 355 extending through the spinal implant in a direction along a longitudinal axis of the spinal implant, the lumen being adapted to permit an elongate member to pass therethrough. In some embodiments, the elongate member comprises a guide wire 356. The guide wire provides the advantage of being able to re-locate the site for repair after first having identified the site with an endoscope or other similar minimally invasive device. Conveniently, in the course of repair surgery, for example using an endoscope or other minimally invasive method, the site of the desired repair can be marked with a guide wire that extends externally. Once the site for repair has been selected and marked, the implant can be fed onto the wire by passing the implant over the end of the wire outside the patient via the lumen 355. The implant can then be passed down the guide wire directly to the site to be repaired simply by sliding the implant along the wire.

Figure 37A:
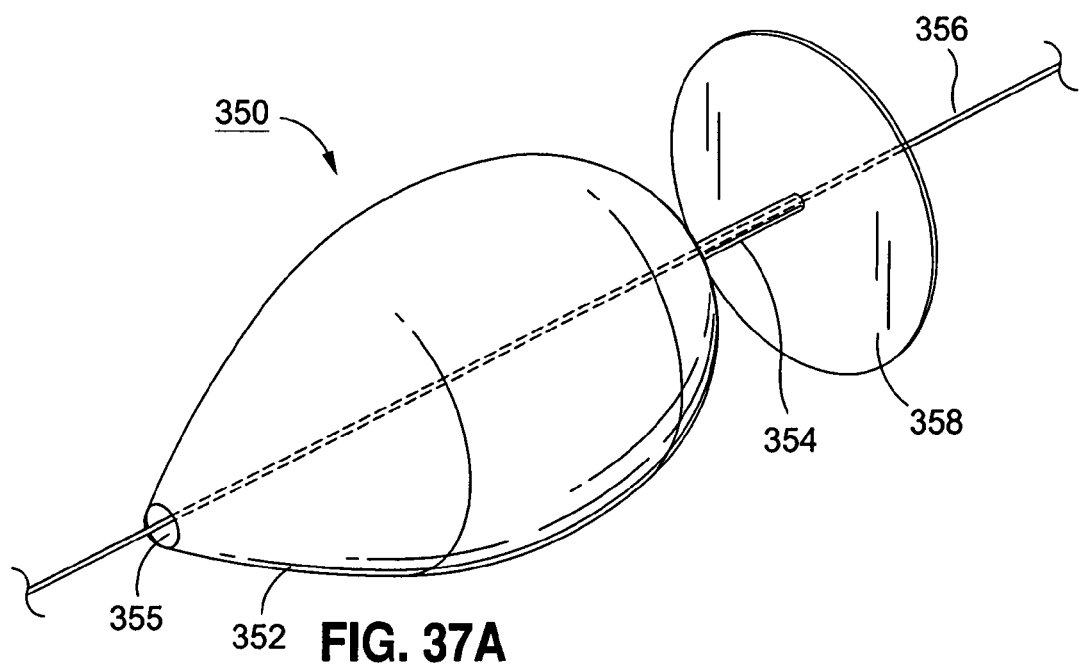
FIG. 37 illustrates a front perspective view of a spinal implant with a centrally located hole for placement of the implant with a guide wire, and thin tail segment (A), and the device implanted within the disc (B).
Figure 37B:
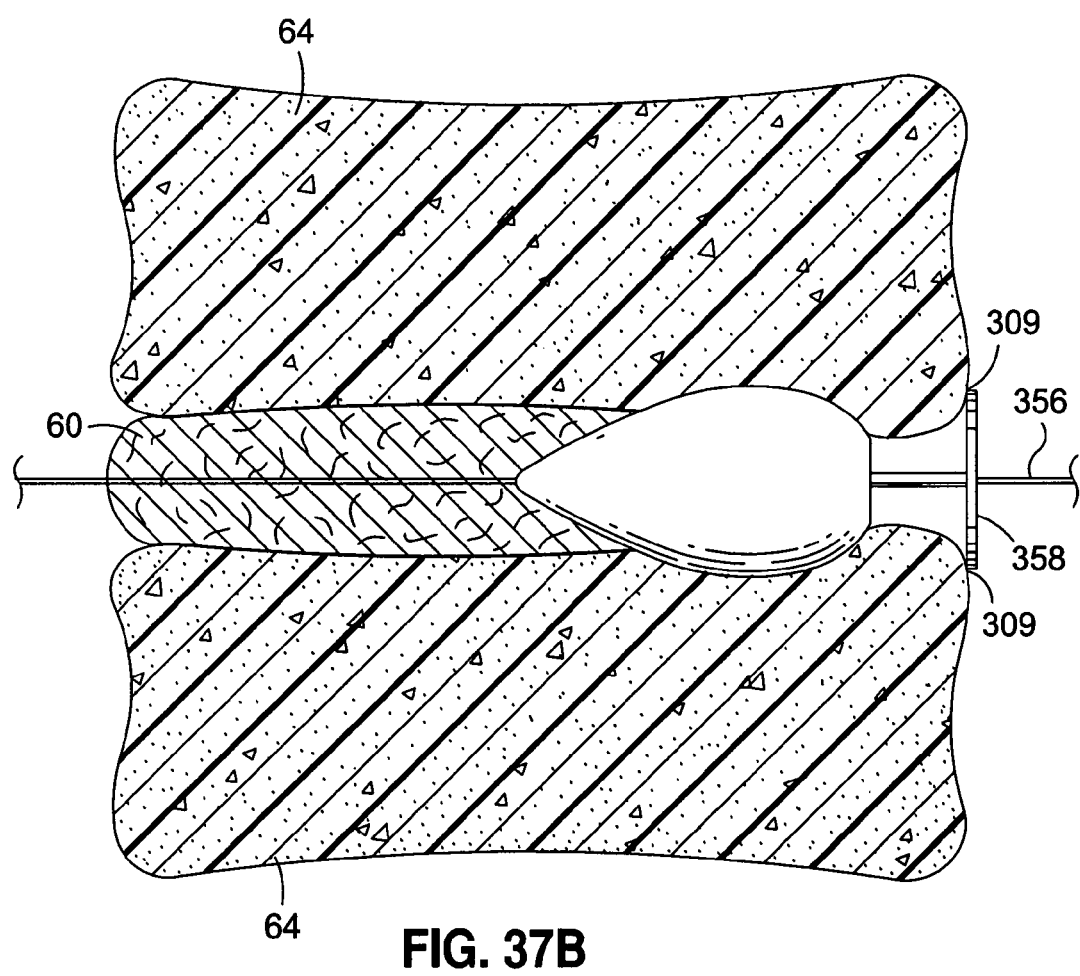

In certain embodiments compatible with a guide wire, one of which is depicted in FIG. 37B, an implant 350 is shown with a relatively thin tail segment 354, the head and tail both including an axially located a lumen 355 extending through the spinal implant in a direction along a longitudinal axis of the spinal implant, the lumen being adapted to permit an elongate member to pass therethrough. In some embodiments the elongate member comprises a guide wire 356. The tail flange 358 abuts the extradiscal lips 309 of adjacent vertebrae. The tail segment comprises a thin flexible material of sufficient tensile strength such that some radial movement is possible between the head and tail flange, but where the relative distance along the longitudinal axis between the two portions of the implant is maintained. Providing a thin and flexible tail segment would thus permit some movement of the head portion relative to the tail flange, potentially improving spinal mobility, without compromising either the anchoring and spacer functions of the head portion, or the barrier function of the implant.

As before, optionally providing a hole down the longitudinal axis of the implant permits the use of a guide wire for routing or advancing the implant to the repair site using a minimally invasive method. The flexible tail portion will permit accommodation of some radial movement of the head portion relative to the tail portion, as might be expected with flexure of the spine, and thus would be operative to help maintain the tail flange 358 relatively in place with respect to the extradiscal lips 309 of adjacent vertebrae thus improving the barrier function of the tail flange.

Figure 38:
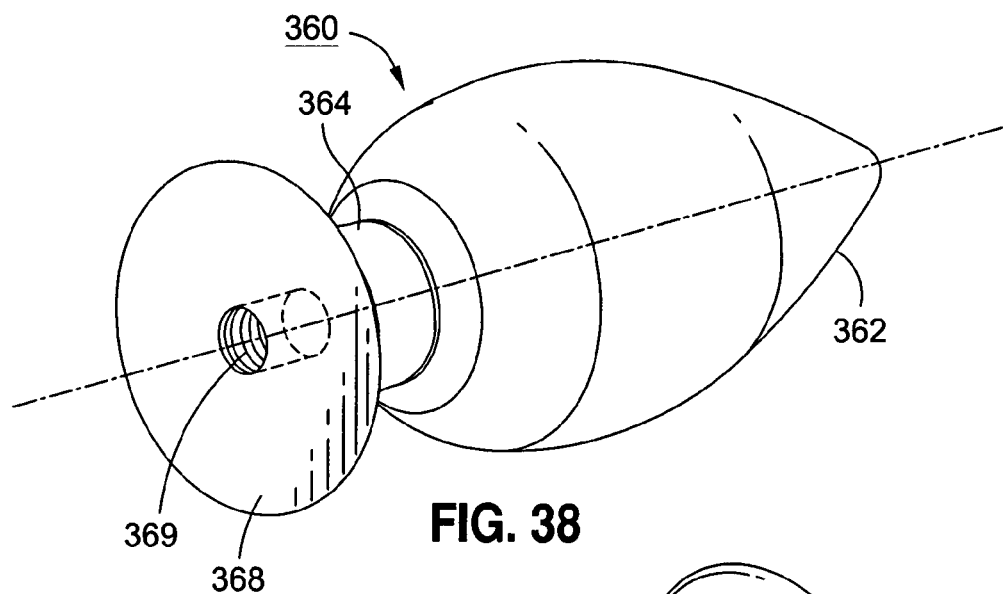
FIG. 38 illustrates a front perspective view of a spinal implant with a threadable tail piece.
Figure 39:
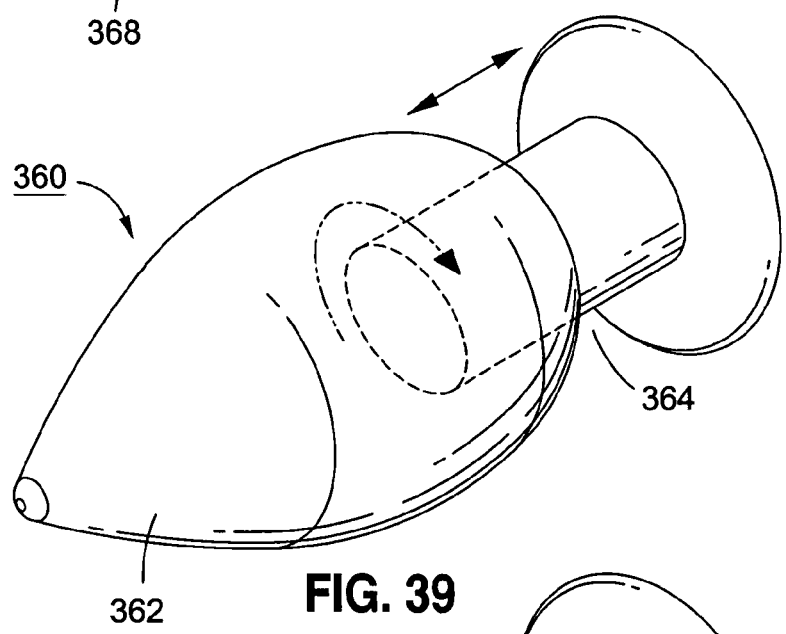
FIG. 39 illustrates a front perspective view of a spinal implant with an insertable tail piece.

In some embodiments the spinal implant comprises a plurality of components that are reversibly coupled, being assembled either prior to implantation, or as part of the implantation procedure, into the completed implant device. For example, FIGS. 38 and 39 depict an implant 360 comprising a head portion 362 into which a separate tail segment 364 or alternatively a separate tail flange 368 are reversibly coupled. For example, as shown in FIG. 38, the tail flange 368 could be separate from the tail segment 364 and head portion. In this instance the tail flange would be threaded onto a bolt-like extension 369 that would extend from the tail segment 364. Alternatively, the tail segment and tail flange comprise a contiguous piece that engages a separate head portion as is shown in FIG. 39. In each of these cases, providing a mechanism for threading together the head and barrier portions provides a means for better securing the tail flange against the extradiscal lips of adjacent vertebrae, thus providing an improved barrier function to prevent extrusion of material, in particular the nucleus pulposus, from the intervertebral disc space. Although not illustrated, certain embodiments like those illustrated in FIGS. 38-39 could include a hole located substantially along the longitudinal axis in order to permit placement of the implant using a guide wire.

For embodiments of the present spinal implant comprising separate portions, the engagement means might be reversibly coupled by compatible threads, or other coupling mechanisms such as, but not limited to, a spring latch, bayonet mount, pin and detent, and the like. In some embodiments the components of the spinal implant can be lockably coupled in order to prevent inadvertent separation after placement. For example, the head portion can be lockably couple to the barrier portion. In these cases there can be provided a twist-and-lock arrangement, or other similar means of lockably connecting the pieces.

An advantage is provided by reversibly coupled and lockably coupled embodiments in that the head portion can be placed in the prepared implantation site, and then the barrier portion subsequently coupled. It is a further advantage of such an arrangement that the tail flange will be brought into a very snug abutment relative to the extradiscal lips of adjacent vertebrae, thereby better securing and ensuring the stability of the implant. A variety of possible means with which to reversibly couple or lockably couple separate head and barrier portions are well known in the art and could include, without limiting the invention, such means as threads, clips, spring-loaded ball bearing and groove combinations, biocompatible adhesives, or any other suitable means for connecting the two pieces in a secure fashion.

Figure 40:
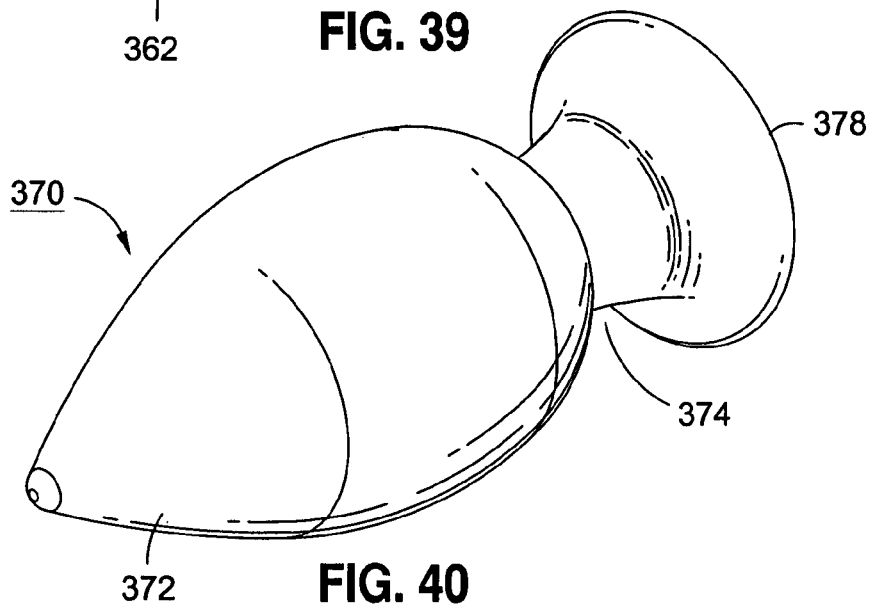
FIG. 40 illustrates a front perspective view of a spinal implant with head and tail portions made from different materials.
Figure 41A:
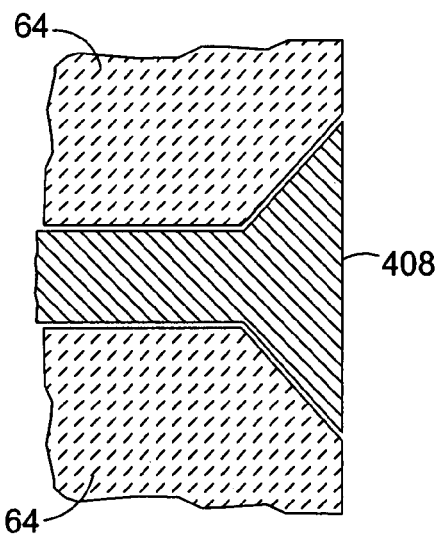
FIG. 41 A-E are side views of spinal implants with variously shaped tail flanges, implanted within the disc.
Figure 41B:
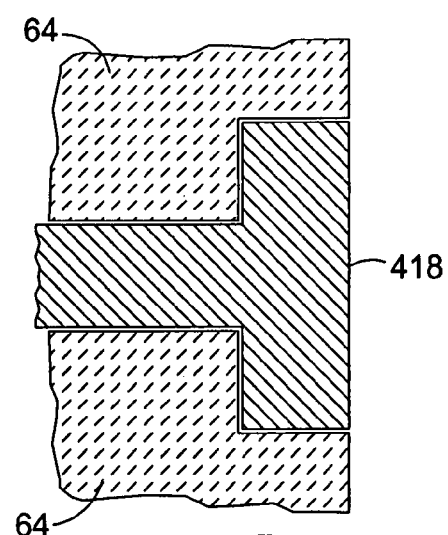
Figure 41C:
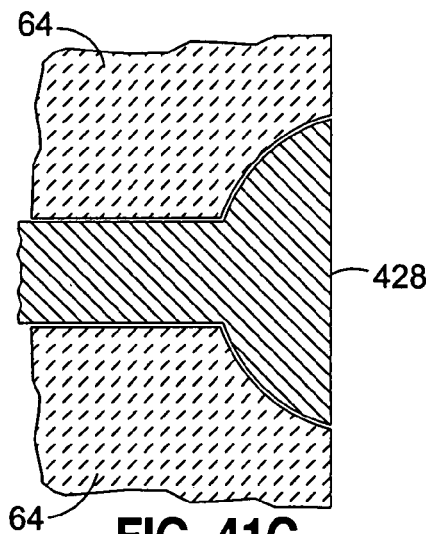
Figure 41D:
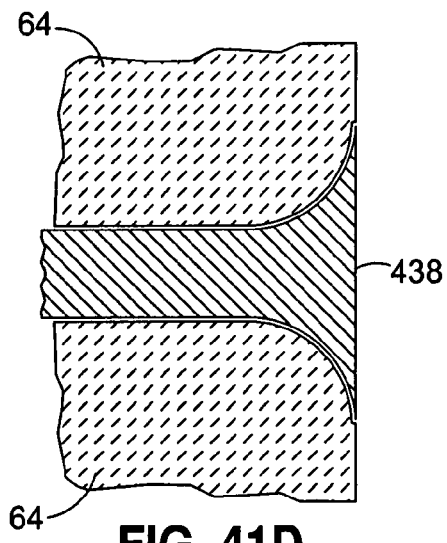
Figure 41E:
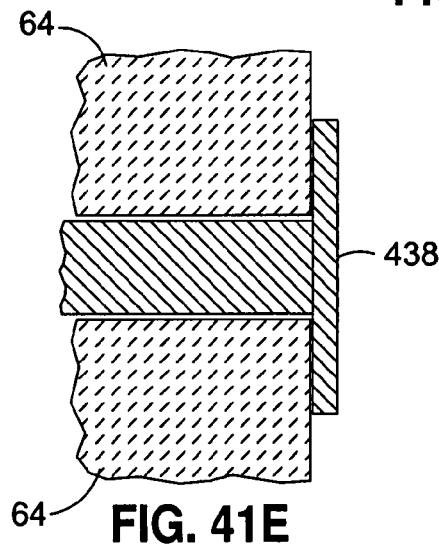

It is further realized that the various functional domains spinal implant of the invention need not be fashioned from a single material. As the head portion, tail segment and tail flange can perform different functions, there might be a potential advantage in fashioning these different functional domains of the implant from materials best suited to perform a particular function. For example, in some embodiments of the spinal implant 370, it can be desirable to provide a head portion 372 that is resilient and approximates the biomechanical properties of the native intervertebral disc. The resiliency can be derived from material selection, from structural members such as cantilever springs, or from a combination of structural and material features. The tail segment 374 might be fashioned of a material that is more flexible to allow greater mobility of the spine without compromising the structural integrity provided by the implant. Likewise, in some embodiments, the tail flange 378 can perform optimally if it is fabricated from a more rigid material that resists deformation in order to better carry out its barrier function, as in FIG. 40.

Thus, while the shape and design of the spinal implant can be varied, the various parts of each of these embodiments still perform the same basic functions. Namely, the head portion abuts and supports facing endplates of the first and second vertebral discs to aid in preventing collapse of the intervertebral disc while providing dynamic stability to the motion segment. The head portion further performs a spacer function, maintaining adjacent vertebrae at a relatively constant distance from each other, at least at the site of the herniation being repaired. The tail portion abuts and supports the facing endplates to aid in preventing collapse of the intervertebral disc while providing dynamic stability to the motion segment. In addition, the tail flange abuts the extradiscal lips of the first and second discs to prevent the implant from penetrating the disc beyond a certain pre-determined amount.

As described above certain embodiments of the invention also provide methods of preparing the implantation site. To better secure the spinal implant in place, in certain embodiments it is desirable to ream the extradiscal lips of adjacent vertebrae in order to match the shape of the tail flange on the implant. The reaming method (i.e. countersinking) is thus beneficial to improve the complementarity of the fit between the implant and the implantation site. By reaming, or other complementary fit-generating process, the implant can be effectively countersunk into the adjacent vertebrae, thus limiting protrusion of the implant from the surface of the spine, without limiting its function. Some exemplary embodiments are shown in FIG. 41A-D. A variety of tail flange shapes are compatible with a countersinking method.

Alternatively, and as shown in FIG. 41. E, the site can be prepared to receive the implant without countersinking. In either the countersunk or non-countersunk configurations, the tail flange still operates as an externally located barrier relative to the intervertebral disc to prevent loss of material, in particular nucleus pulposus from the interior of the disc.

Several possible general shapes are possible for the tail flange and countersunk region on the vertebrae. In one embodiment, FIG. 41A, the tail flange 408 has a constant rate taper. In one embodiment, FIG. 41B the tail flange 418 is not tapered but rather is relatively squared. In one embodiment, FIG. 41C, the tail flange 428 comprises a curved taper that is generally convex in shape, while in one embodiment, FIG. 41D, the tail flange 438 comprises a curved taper that is general concave in shape. The present invention is also compatible with a tail flange that is not countersunk 448, FIG. 41E, and which simply abuts the extradiscal lips of adjacent vertebrae, thereby providing an external barrier that prevents extrusion of material from within the intervertebral disc. The illustrated examples are included merely to illustrate some possibilities without intending to be limited to the precise shape and/or size depicted. Various degrees of taper or thickness of the tail flange are also possible and the invention is not meant to be limited in any way to the specific examples presented herein.

While not essential for the functioning of the spinal implant, countersinking provides an advantage in that it permits better engagement of the tail flange and the adjacent intervertebral discs, as well as to better prevent inward movement of the implant. Additionally, countersinking permits a substantially flush fit of the tail flange along the exterior surface of the discs, which can limit pressure on other anatomical structures in the vicinity of the repair site.

Figure 42A:
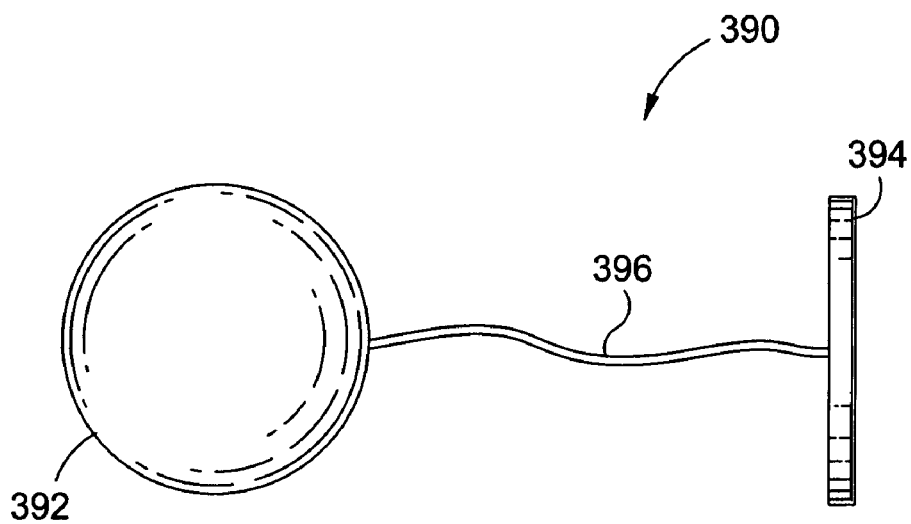
FIG. 42 A-D are side views of spinal implants comprising a head portion and tail portion coupled by a flexible tether.
Figure 42B:
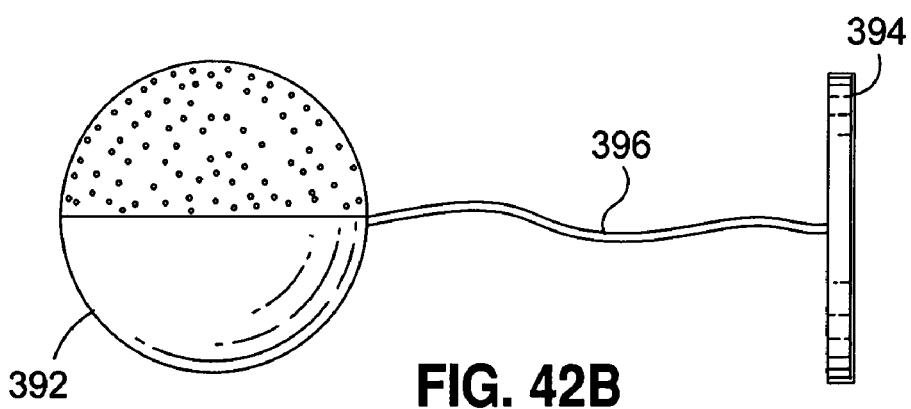
Figure 42C:
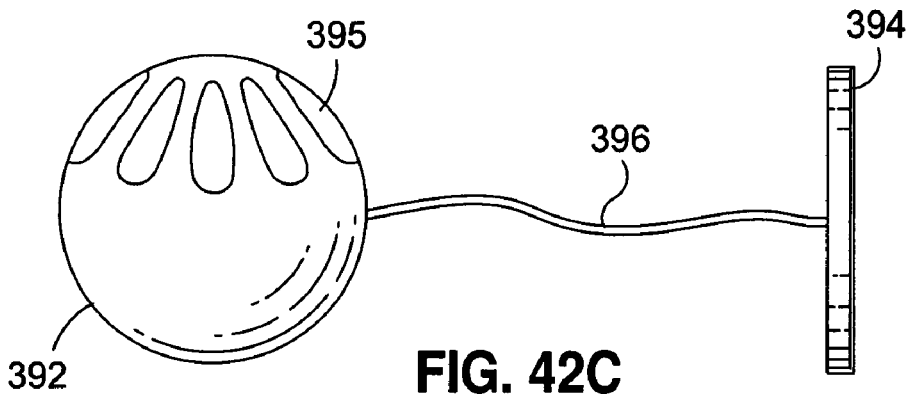
Figure 42D:
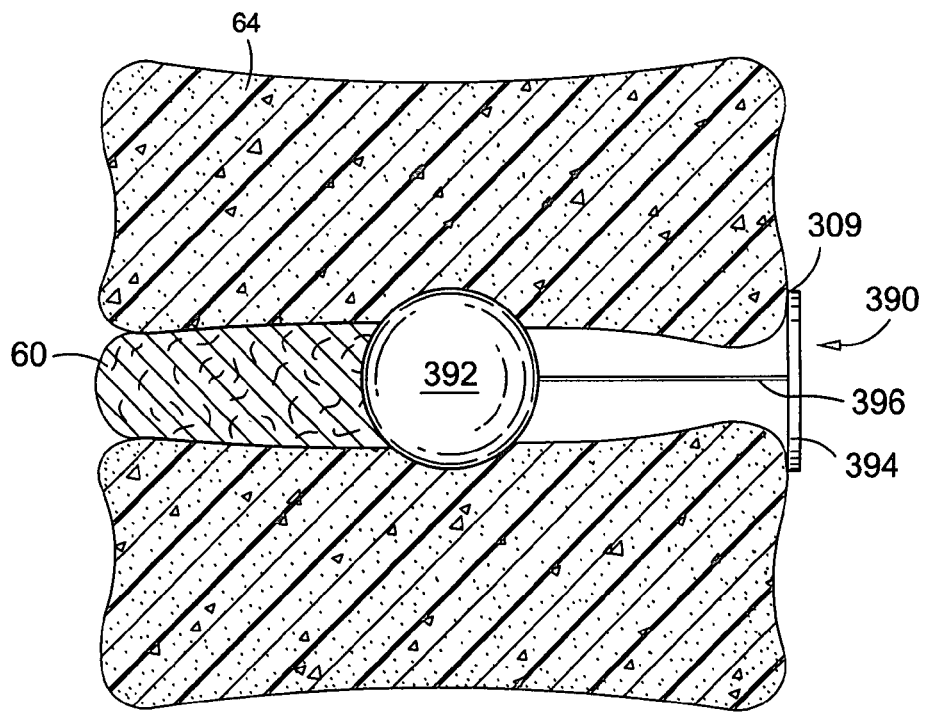

In some embodiments, as illustrated in FIG. 42A, the spinal implant 390 can comprise a head portion 392 and a barrier portion 394, coupled by a flexible tether 396. The head portion 392 can be constructed of more than material as shown in FIG. 42B. or may have bone compaction holes 395 as in FIG. 42C. Having a flexible tether permits movement of the barrier portion and the head portion relative to each other and yet provides that the head portion and barrier portion each remain substantially located in a stable position relative to the intervertebral disc, the adjacent vertebrae, and the repair site, as illustrated in FIG. 42D. The illustration in FIG. 42D is but one embodiment of an implant with a flexible and is not meant to limit the scope of the invention. A variety of shapes, sizes, and compositions of head and barrier portions are possible and will be readily apparent to those skilled in the art. Furthermore, the tether can be any of a number of flexible substances including monofilaments, braided lines, and the like. The size, shape and length of the tether and the materials from which it is constructed are not limiting to the scope of the invention.

Providing a flexible tether can enhance mobility of the spine without compromising the function of each portion of the implant. Thus the head portion remains effective as a spacer, effectively supporting the adjacent vertebrae, and the barrier portion remains effective to prevent substantial extrusion of material from the intervertebral disc, for example nucleus pulposus.

Figure 43:
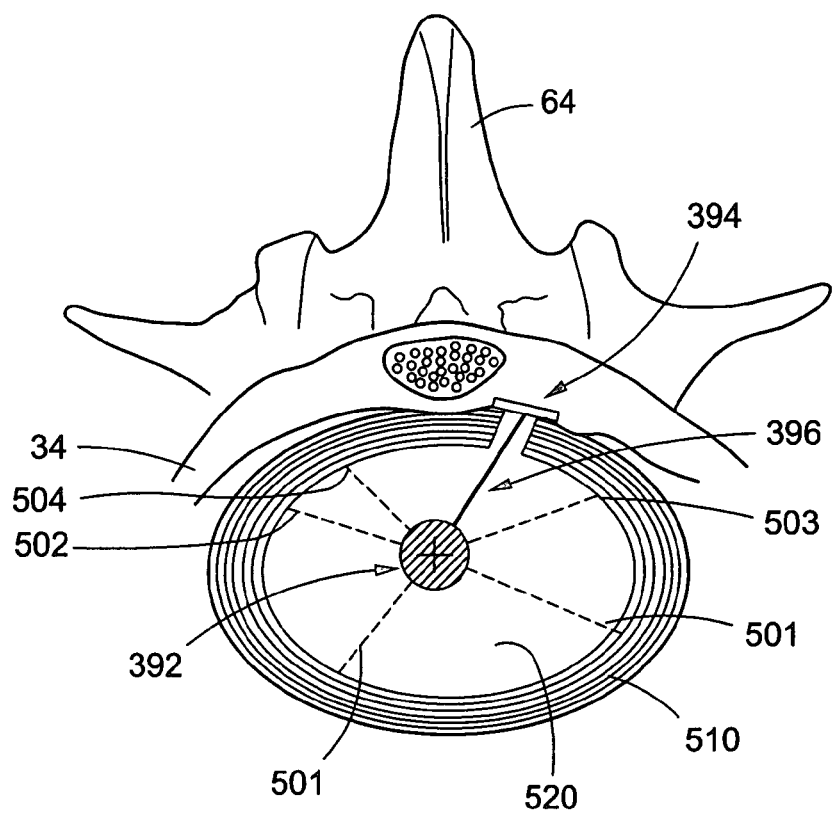
FIG. 43 is an axial view of the spinal implant of FIG. 42 implanted in a spine.

Providing a tether further increases the functional flexibility of the spinal implant with respect to implantation locations. For example, as shown in FIG. 43, where the barrier portion 394 has been placed at a site of herniation to effectively close it off and prevent extrusion of nucleus from the damaged area, the head portion 392 can conveniently be placed at any one of a number of desired locations, 500, 501, 502, 503, 504 within the intervertebral disc. The dashed lines in FIG. 43 represent the fact that with a flexible tether 396 the head portion 392 can be placed in any one of a plurality of locations along points whose distance from the barrier portion 394 is limited only by the length of the flexible tether 396. Alternatively, as with previously described embodiments the head portion can be placed within the region of the annulus if desired. The choice of a desired site will be made by the surgeon. If desired, with a flexible tether, the head portion can be located in the annulus 510, or in the nucleus 520, while still maintaining the barrier portion 394 in contact with an exterior surface of the intervertebral disc.

Figure 44A:
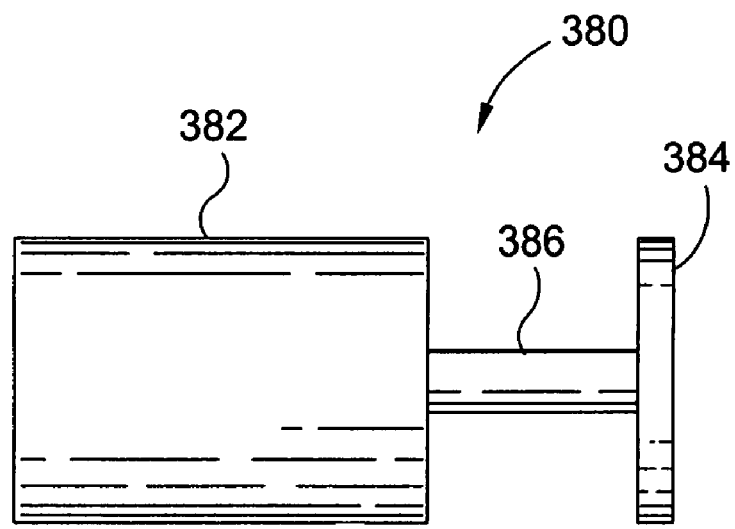
FIG. 44 shows alternative embodiments (A) and (B) of spinal implants without tapered segments, and the devices implanted with the disc (C) and (D).
Figure 44B:
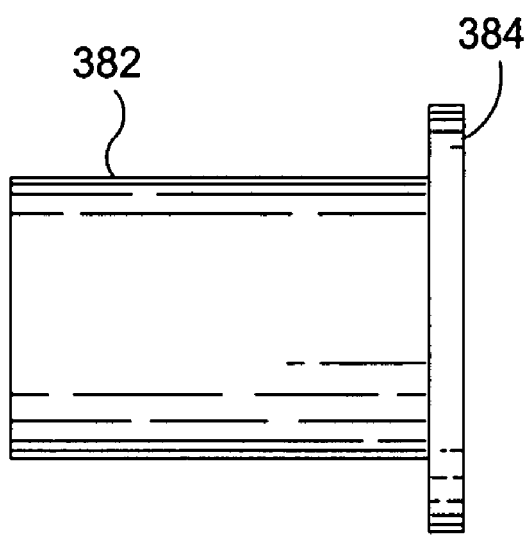
Figure 44C:
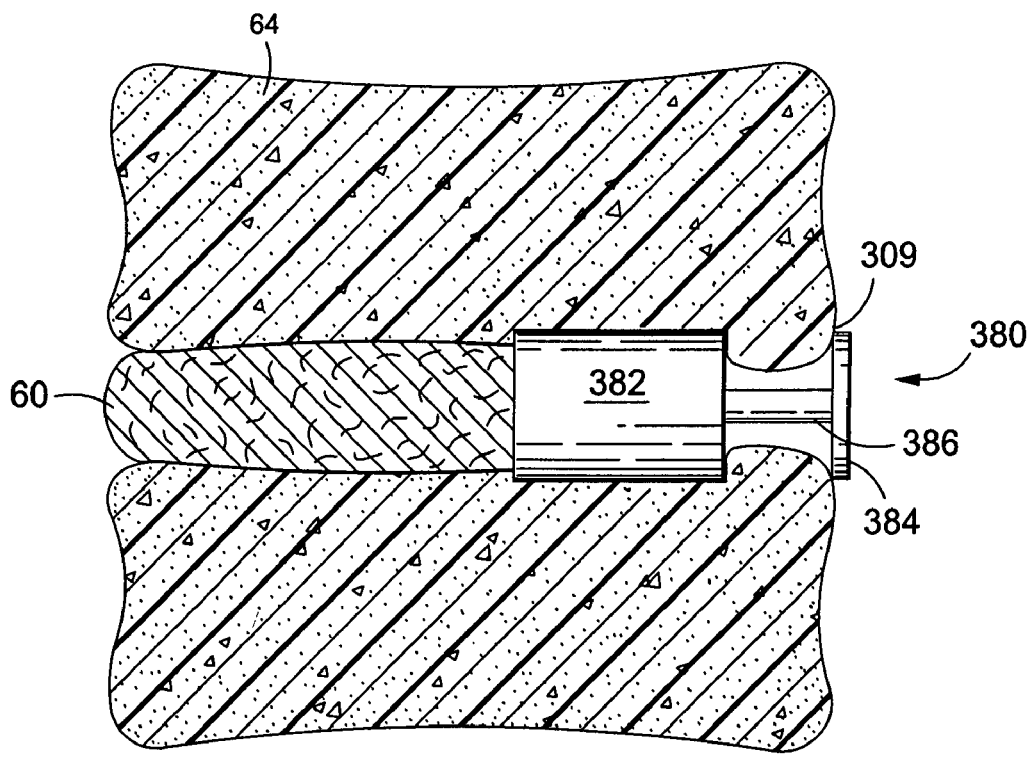
Figure 44D:
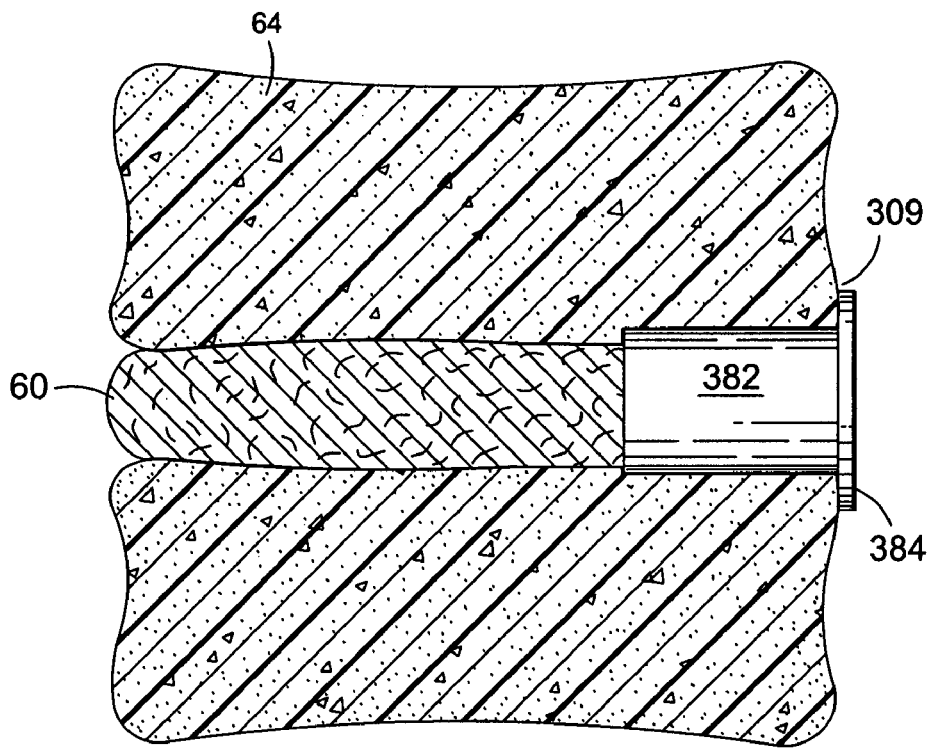

It is also contemplated within the scope of the invention to provide in some embodiments, a spinal implant 380 in which none of the segments comprise a taper. As illustrated in FIGS. 44A and B, an implant 380 that is substantially rectilinear along its longitudinal axis can still provide a head portion 382 and barrier portion 384 that is effective in the repair of an annular defect. The implant 382 can optionally include a tail segment 386 that couples the head portion 382 to the barrier portion 384. Alternatively, as illustrated in FIG. 44B, it is also not essential that there be an intervening segment between the head portion 382 and barrier portion 384, and these two domains can be directly coupled of the spinal implant in order for the implant to function as described herein. Placement of a non-tapered implant is analogous to placement of a tapered implant, as is illustrated in FIGS. 43 C and D.

The above presents a description of the best mode contemplated for carrying out the present spinal implants and methods of providing dynamic stability to the spine, and of the manner and process of making and using them, in such full, clear, concise, and exact terms as to enable any person skilled in the art to which it pertains to make and use these spinal implants and methods. These spinal implants and methods are, however, susceptible to modifications and alternate constructions from that discussed above that are fully equivalent. Consequently, these spinal implants and methods are not limited to the particular embodiments disclosed. On the contrary, these spinal implants and methods cover all modifications and alternate constructions coming within the spirit and scope of these spinal implants and methods are as generally expressed by the following claims, which particularly point out and distinctly claim the subject matter of these spinal implants and methods.

What is claimed is:

1. A method for repairing a defect in the annulus fibrosus of an intervertebral disc located between the end plate of an adjacent upper vertebra and the end plate of an adjacent lower vertebra, said method comprising the steps of:

A) removing a portion of the intervertebral disc to form an intervertebral space;

B) obtaining or providing an implant device that comprises a head portion and a tail portion, wherein;

the tail portion comprises a tail flange; and the head portion comprises a tapered distal segment, a middle segment and a proximal surface, the distal segment having non-parallel upper and lower edges that are closer together at their distal ends than at their proximal ends and the middle segment having upper and lower edges that are parallel to one another;

C) removing bone from the end plates of the adjacent upper and lower vertebrae in a manner that forms contoured surfaces analogous to the shape of the implant device and, thereafter, D) implanting the implant device such that;

i) the head portion resides in the intervertebral space between the areas from which bone has been removed and the proximal surface of the head portion contacts bone of the adjacent upper and lower vertebrae thereby deterring subsequent expulsion of the head portion from the intervertebral space and further thereby resisting any tendency of the upper and lower vertebrae to move closer to one another; and ii) the tail portion protrudes outside of the intervertbral space with the tail flange positioned so as to prevent the implant from being pushed further into the intervertebral space.

2. A method according to claim 1 wherein the adjacent upper and lower vertebrae are distracted or moved away from one another during insertion of the head of the implant device into the intervertebral space.

3. A method according to claim 1 wherein the distal segment of the head portion is conical and the middle segment is cylindrical.

4. A method according to claim 1 wherein bone is removed from the adjacent upper and lower vertebrae to form a posterior vertebral recess having extradiscal lips.

5. A method according to claim 4 wherein outer aspects of the extradiscal lips are contoured to mate with a distal surface of the tail flange.

6. A method according to claim 4 wherein the defect in the disc annulus comes to rest on the tail portion of the implant device thereby preventing nucleus pulposus from subsequently herniating out of the defect.

7. A method according to claim 6 wherein the tail portion of the implant device comprises a cylindrical segment with the tail flange at the proximal end thereof and wherein the border of the defect in the annulus is in intimate contact with the cylindrical segment of the tail portion and the tail flange thus preventing nucleus pulposus from subsequently herniating out of the defect.

8. A method according to claim 1 wherein the implant device blocks the defect in a manner that prevents future herniation of nucleus pulposus out of the defect.

9. A method according to claim 1 wherein the implant device further comprises a lumen passing therethrough, and wherein Step C comprises inserting an elongate member into the intervertebral space and advancing the implant device over an elongate member to a position where the head of the implant device is in the intervertebral space.

10. A method according to claim 9 wherein the elongate member comprises a guide wire.

11. A method according to claim 1 further comprising the step of deploying a tubular guard to prevent surrounding tissue from interfering with or becoming damaged during the performance of the method.

12. A method according to claim 1 wherein the cross-sectional shape of the implant is circular.

13. A method according to claim 12 wherein the cross-sectional shape of the implant is non-circular.

14. A method according to claim 13 wherein the cross-sectional shape of the implant device is selected from: elliptical, rectilinear, triangular, or oval.

* * * * *